US012565314B2

(12) United States Patent
Lepek et al.

(10) Patent No.: US 12,565,314 B2
(45) Date of Patent: Mar. 3, 2026

(54) SYSTEM AND METHOD FOR AUTOMATED COOLING STORAGE TRANSPORT AND RELEASE OF BENEFICIAL INSECTS

(71) Applicant: Senecio Ltd., Kfar-Saba (IL)

(72) Inventors: Hanan Lepek, Kfar-Saba (IL); Dor Elyahu Cohen, Tel-Aviv (IL)

(73) Assignee: Senecio Ltd., Kfar-Saba (IL)

( * ) Notice: Subject to any disclaimer, the term of this patent is extended or adjusted under 35 U.S.C. 154(b) by 185 days.

(21) Appl. No.: 18/032,371

(22) PCT Filed: Oct. 18, 2021

(86) PCT No.: PCT/IL2021/051230

§ 371 (c)(1),
(2) Date: Apr. 18, 2023

(87) PCT Pub. No.: WO2022/079722

PCT Pub. Date: Apr. 21, 2022

(65) Prior Publication Data

US 2023/0389514 A1 Dec. 7, 2023

Related U.S. Application Data

(60) Provisional application No. 63/093,232, filed on Oct. 18, 2020.

(51) Int. Cl.
*B64D 1/16* (2006.01)
*A01K 67/31* (2025.01)
(Continued)

(52) U.S. Cl.
CPC ................ *B64D 1/16* (2013.01); *A01K 67/31* (2025.01); *B64U 2101/45* (2023.01); *B64U 2101/60* (2023.01); *F25D 3/14* (2013.01)

(58) Field of Classification Search
CPC ... B64D 1/16; B64D 1/10; B64D 1/12; B64U 2101/45; B64U 2101/60; A01K 67/31; A01K 67/30; F25D 3/14
See application file for complete search history.

(56) References Cited

U.S. PATENT DOCUMENTS 3,468,289 A * 9/1969 Broida ................. B65D 81/266
                                                              119/6.5
5,895,310 A * 4/1999 Otomo ................... A01K 47/06
                                                              449/20
(Continued)

FOREIGN PATENT DOCUMENTS

JP        3848625        9/2006
WO   WO 2021/188054    9/2021
WO   WO 2022/079722    4/2022

OTHER PUBLICATIONS

International Preliminary Report on Patentability Apr. 27, 2023 From the International Bureau of WIPO Re. Application No. PCT IL2021/051230. (8 Pages).

(Continued)

*Primary Examiner* — William L Gmoser

(57) ABSTRACT

An insect distribution device to be carried by drone to distribute insects from the air, comprises a source of passive cooling; an insect chamber; one or more insect containers in said insect chamber; and a release point. The source of passive cooling is in thermal contact with the insect chamber to keep the insect container below a predetermined temperature to keep said insects passive during storage. The device is designed to feed the insect containers in turn to the release point for aerial release.

27 Claims, 32 Drawing Sheets

(51) Int. Cl.
    B64U 101/45          (2023.01)
    B64U 101/60          (2023.01)
    F25D 3/14            (2006.01)

(56)                    References Cited

U.S. PATENT DOCUMENTS

|  |  |  |  |  |
|---|---|---|---|---|
| 8,408,164 | B2 | 4/2013 | Robinson, Jr. | |
| 8,967,029 | B1 * | 3/2015 | Calvert | A01K 67/30 |
| | | | | 239/8 |
| 10,278,368 | B1 * | 5/2019 | Peeters | A01K 1/031 |
| 10,568,309 | B2 * | 2/2020 | Massaro | A01K 67/30 |
| 10,750,733 | B1 * | 8/2020 | Garner | A01M 5/02 |
| 11,700,843 | B2 * | 7/2023 | Zha | A01M 1/026 |
| | | | | 705/7.11 |
| 2017/0280678 | A1 * | 10/2017 | Jones | A01K 5/0291 |
| 2019/0092471 | A1 * | 3/2019 | Lepek | A01K 67/31 |
| 2019/0141969 | A1 * | 5/2019 | Massaro | F42B 12/56 |
| | | | | 43/1 |
| 2020/0154686 | A1 * | 5/2020 | Lepek | G06N 3/08 |
| 2020/0296920 | A1 | 9/2020 | Behling et al. | |
| 2022/0330514 | A1 * | 10/2022 | Jozefiak | A01K 67/30 |
| 2023/0406500 | A1 * | 12/2023 | Tamir | B64D 1/18 |

OTHER PUBLICATIONS

International Search Report and the Written Opinion Dated Feb. 10, 2022 From the International Searching Authority Re. Application No. PCT/IL2021/051230. (11 Pages).

* cited by examiner

Drone
60

Inlet/outlet fan
62

Mountable Release system
64

Release system frame
64

Cold source chamber
42

Inlet/outlet fan
62

Target chamber:
Storage - Insects storage
and release area
44

Release system frame
64

Cold source chamber
42

Dry Ice vent
Temp and
gas evacuator
66

Storage - Insects storage
and release area
44

Inlet/outlet fan
62

Carousel 82.1

82.2

Release fan mounting 88

Insects canisters 84

Release fan 86

Release chamber 90

Inlet/outlet fan 62

80

Insects canisters 84

Carousel

Release fan mounting 88

Surface of Release insects chamber

Release fan 86

Release chamber 90

Release fan

Inlet/outlet fan 62

Carousel cover 106

Carousel 82

Shaft 92

Holding frame 98

Surface of Release insects chamber 104

Release hole 102

Carousel floor

Release chamber 90

Release fan 86

Release chamber 90

Release hole 100

Surface of Release insects chamber

Carousel 82

Inlet/outlet fan 86

Release hole 100

Release chamber 90

106 — Carousel cover

Carousel shaft

116 — Carousel floor

92

88

86

Cavities in the carousel body (the insect storage unit), serve as canister holders for canisters

112

Carousel body

110

Mounting position (position for shaft)

114

Release fan
86

Carousel
82

Cavities holes (serve as canisters holes)
112

Shaft
92

Motor
94

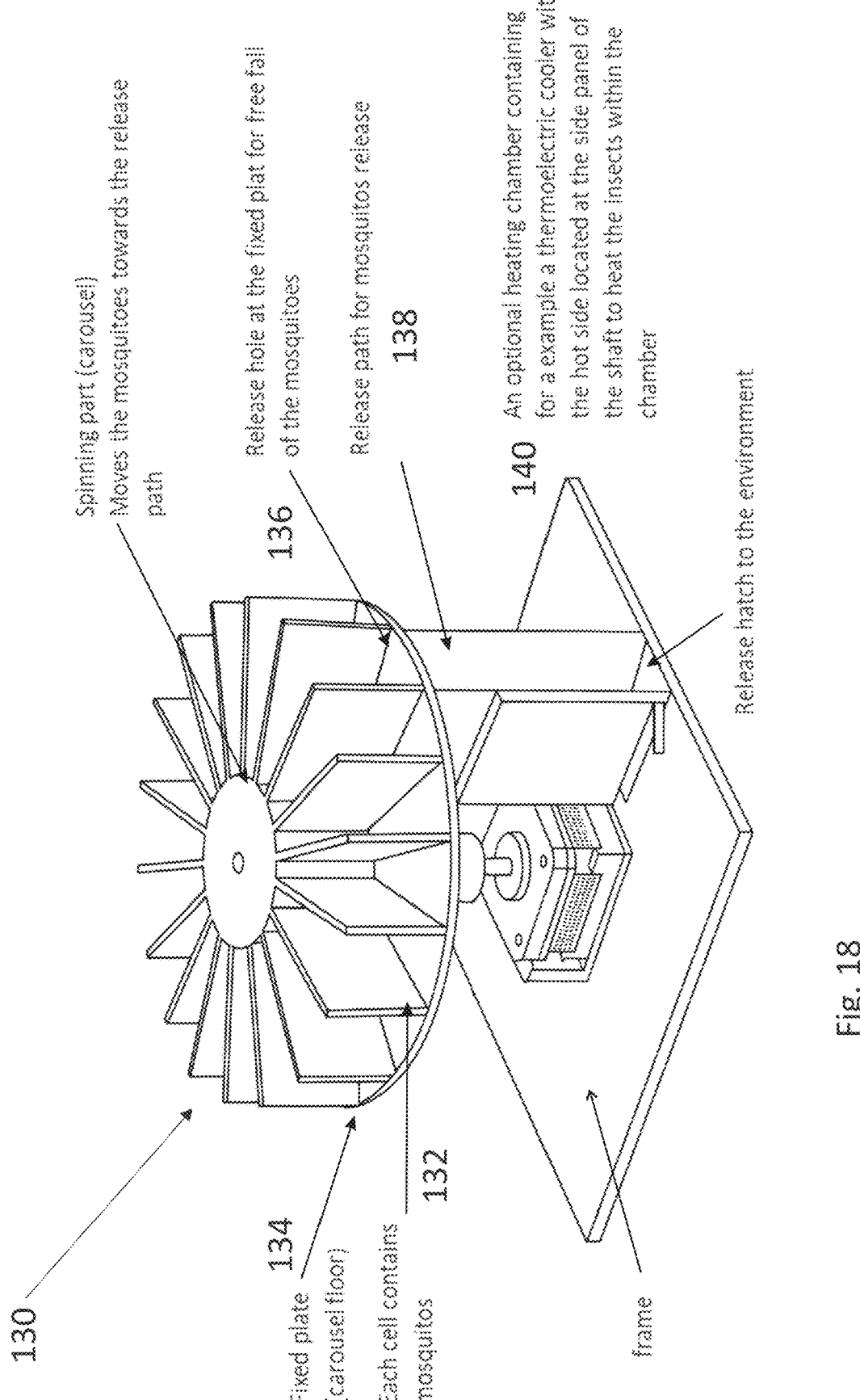

Spinning part (carousel)
Moves the mosquitoes towards the release path

Release hole at the fixed plat for free fall of the mosquitoes

Release path for mosquitos release

138

An optional heating chamber containing for a example a thermoelectric cooler with the hot side located at the side panel of the shaft to heat the insects within the chamber

140

Release hatch to the environment

136

130

134

Fixed plate (carousel floor)

Each cell contains mosquitos

132 frame

Fig. 18

154    Fan inlet-inserting cold air from chilled cabin (cold source)

Conveying mechanism to convey insects towards release shaft

Shaft for mosquitos release

Release hatch to the environment

150

Closed box
152

Fixed plate

Insect storage cells

160 mosquitos in each cell
being conveyed towards
he release hatch

162

164
Release hatch to
the environment

170

172

174

176

176

Canister with
doors

174

Heating chamber

176

Heating
elements      182

Heating
chamber      178
shutter

Actuator      180

Cold source chamber

Release system for dropping biodegradable cans

198

190

Heat Transfer

Dry Ice

196

194

Dry Ice holders

Canister sleeve for holding and guiding canisters as they drop out

200

Release position

202

Actuators

214

Inlet/outlet fan

Release can/canister

192

Release position

202

Release canister 192

Canister sleeve 200

Release position

Release door 216

Actuator

Release canister 192

Canister sleeve 200

Actuator 204

Release door 216

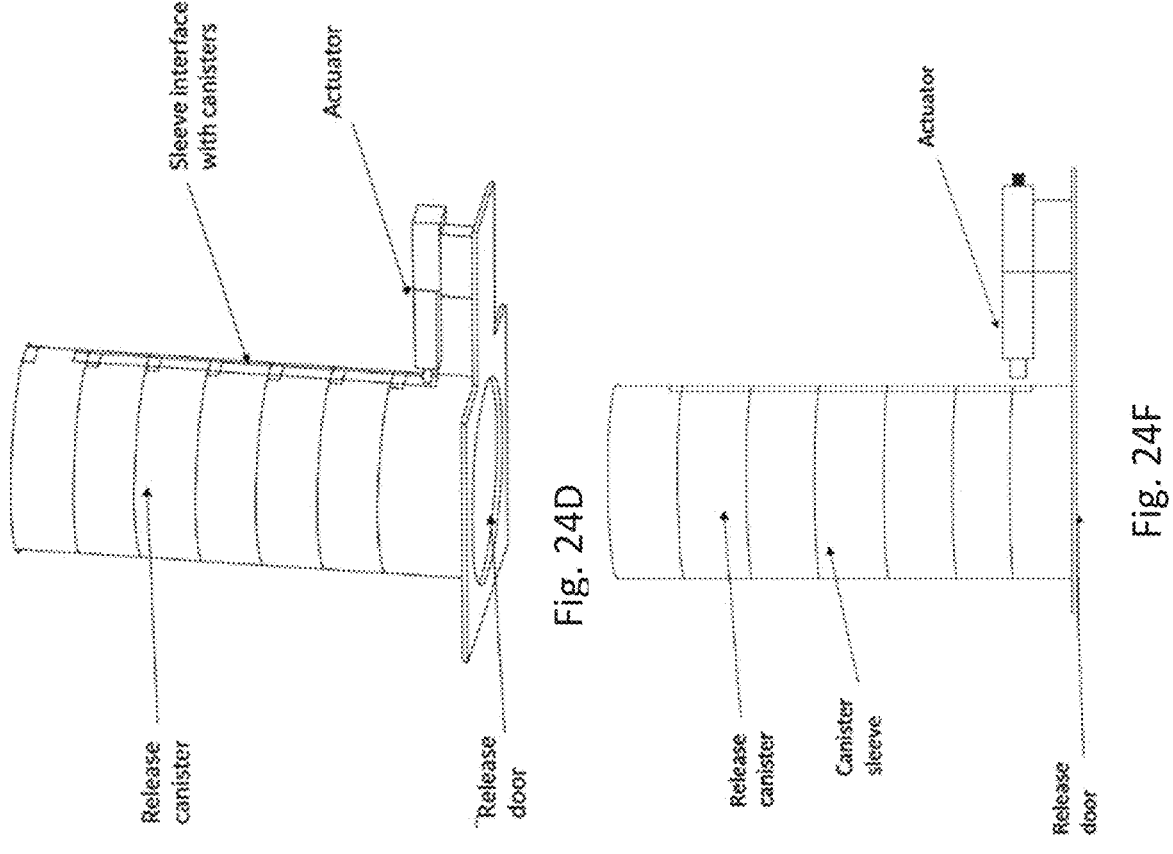
Fig. 24C
Fig. 24D
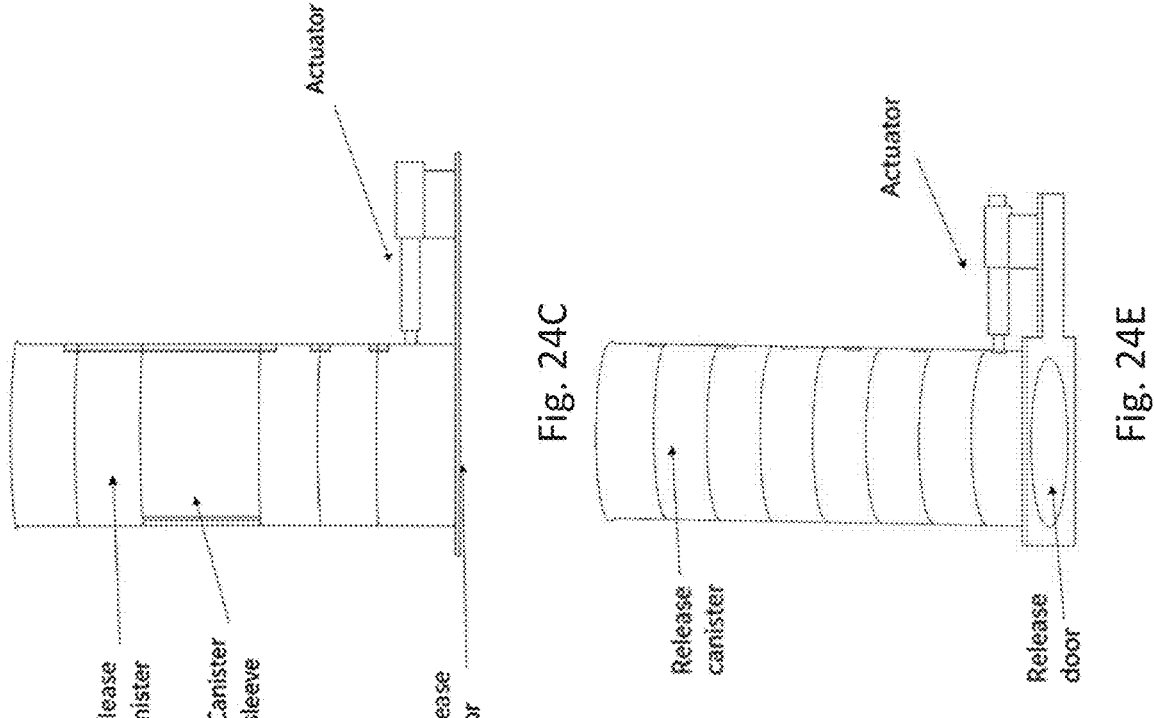
Fig. 24E
Fig. 24F

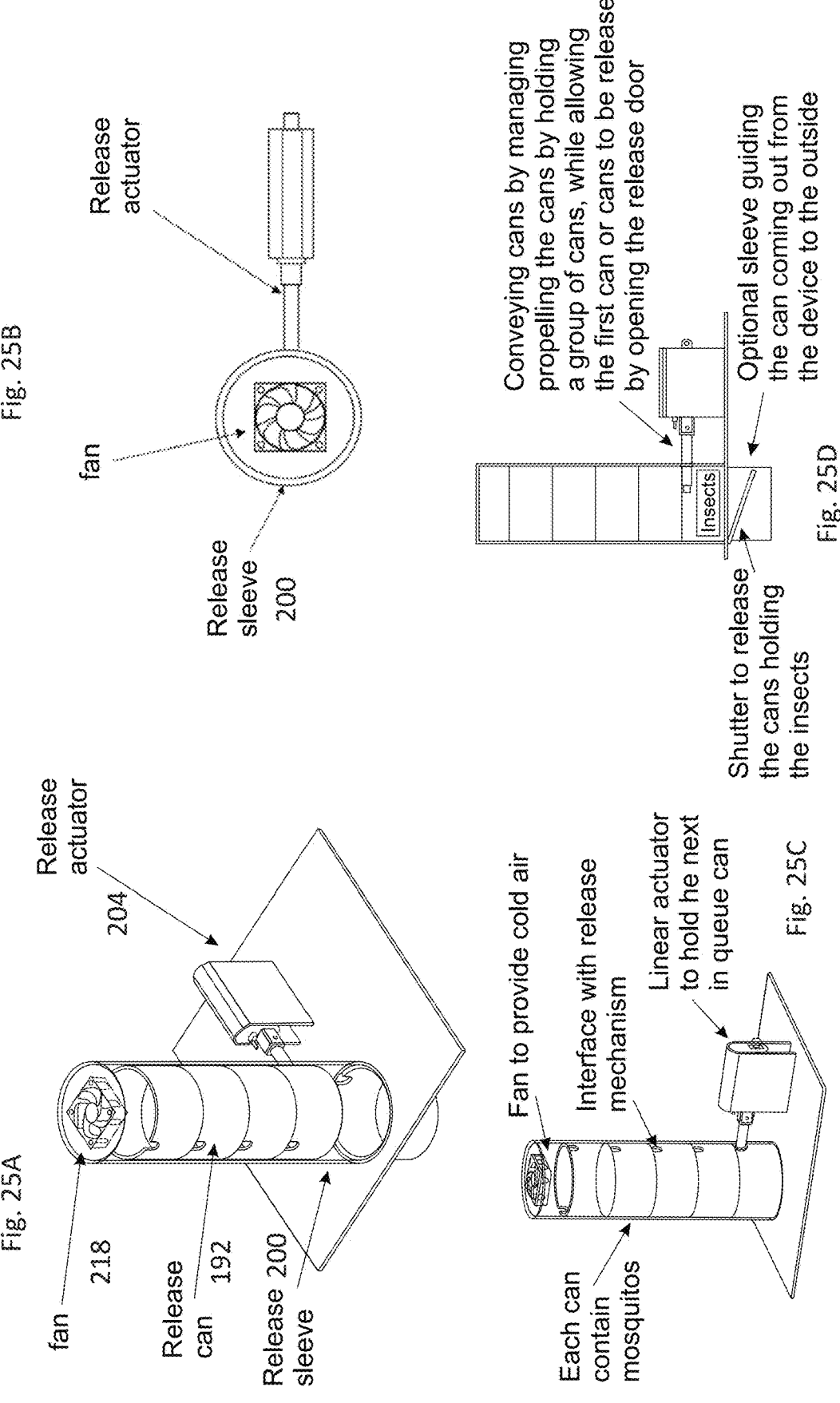

Fig. 25B

Release actuator fan

Release sleeve 200

Fig. 25A

Release actuator

204 fan

218

Release can 192

Release 200 sleeve

Fig. 25C

Fan to provide cold air

Interface with release mechanism

Linear actuator to hold he next in queue can

Each can contain mosquitos

Fig. 25D

Conveying cans by managing propelling the cans by holding a group of cans, while allowing the first can or cans to be released by opening the release door Optional sleeve guiding the can coming out from the device to the outside Shutter to release the cans holding the insects Insects Ice Pack
252

Cold temperature source
within the same unit

Release system wit a conveying
mechanism to convey insects
towards release position
250

Fan to enable inlet/outlet
of air to control the
temperature

Mosquito storage inside release tubes

262

260

264

266

Container, with closed closure, for holding dry ice

Container, with open closure, for holding dry ice

Fig. 29

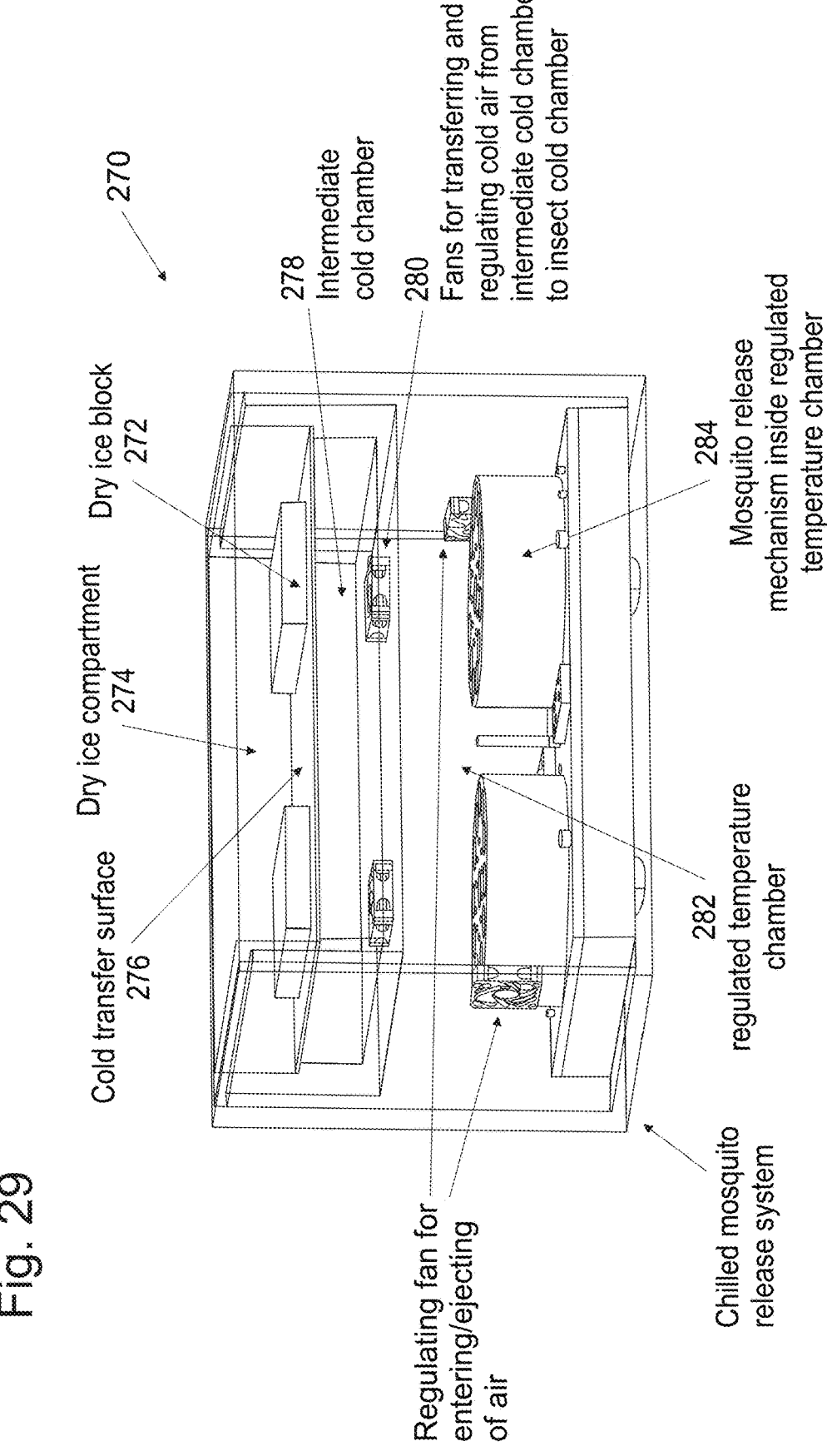

270

Dry ice block
272

Intermediate
cold chamber
278

Fans for transferring and
regulating cold air from
intermediate cold chamber
to insect cold chamber
280

Dry ice compartment
274

Cold transfer surface
276

Mosquito release
mechanism inside regulated
temperature chamber
284 regulated temperature
chamber
282

Regulating fan for
entering/ejecting
of air

Chilled mosquito
release system

Fans for transferring and ejecting external air to regulate the temperature 298

Dry ice compartment (small circles) 296

Mosquito storage inside release tubes (larger circles) 294

290

Dry ice block
302

Dry ice compartment
304

Cold transfer surface
306

310
Multiple heating
units, heat the
mosquito chamber
in order to increase
temperature thereby
to regulate the mosquito
chamber temperature 308
Mosquito release
mechanism inside regulated
temperature chamber Chilled mosquito
release system 300

Temperature measurement sensor, to support regulating the cold chamber temperature (e.g. when to start and stop the fans, or when to start and stop heating elements)

Piston pushing insects downwards and out of the ejection hole

312

Release carousel with insects in each tube

310

Cold surface
322

324

Dry ice
320

Release carousel with insects in each tube

326

Opening with a closure mechanism to regulate incoming air instead of using an active fan.

330

328

Door in its open position (actual mechanism to change door position is not drawn Dry ice

324

326

320

322

Chilled insects
release device

Cold insect
storage unit with
release tubes

Ejection hole for
chilled insects

Fans for regulating the
temperature

Fan for blowing
insects out

SYSTEM AND METHOD FOR AUTOMATED COOLING STORAGE TRANSPORT AND RELEASE OF BENEFICIAL INSECTS

RELATED APPLICATIONS

This application is a National Phase of PCT Patent Application No. PCT/IL2021/051230 having International filing date of Oct. 18, 2021, which claims the benefit of priority under 35 USC § 119(e) of U.S. Provisional Patent Application No. 63/093,232 filed on Oct. 18, 2020.

The contents of the above applications are all incorporated by reference as if fully set forth herein in their entirety.

FIELD AND BACKGROUND OF THE INVENTION

The present invention, in some embodiments thereof, relates to a system and method for automated cooling storage transport and release of beneficial insects and, more particularly, but not exclusively, to such a system for use with drones.

Sterile Insect Technique campaigns require the release of millions of insects over areas that may be measured in square miles. Releasing insects on the ground is a tedious job and requires a lot of manpower. Yet, in order to release large numbers of insects from a flying drone, solutions are required regarding such issues as how to release the insects, and how to store the insects while they are immobilized, at the same time causing minimal damage to the insects. Furthermore the solution has to be relatively light weight due to weight limits.

In order to maximize efficiency and lower the number of flights and required number of drones, drones capable of carrying tens or dozens of thousands up to hundreds of thousands of beneficial insects such as sterile mosquitoes or sterile fruit flies and other beneficial insects are required. Currently no such storage solution as described below for usage with drones exists.

SUMMARY OF THE INVENTION

Embodiments may provide a container for insects which is combined with a source of passive cooling that keeps the insects in a dormant stage during drone flight. The passive cooling may be dry ice and the dry ice may be kept in a separate compartment from the insects, the two compartments being in thermal contact.

According to an aspect of some embodiments of the present invention there is provided an insect distribution device for carrying by drone to distribute insects from the air, the device comprising:

a source of passive cooling;

an insect chamber;

at least one insect compartment in the insect chamber;

at least one release point; wherein the source of passive cooling is in thermal contact with the insect chamber to keep the at least one insect compartment below a predetermined temperature, the predetermined temperature selected to keep the insects passive during storage, the device being configured to cause the at least one insect compartment to reach the release point for aerial release.

In this description and claims, the term passive cooling refers to use of cold material such as ice, dry ice, liquid helium and the like as sources of cold. The term is to be contrasted with active cooling as in powered refrigeration.

In embodiments, the source of passive cooling comprises dry ice.

Embodiments may comprise a cooling chamber, the source of passive cooling being located in the cooling chamber.

The cooling chamber may have a thermal conductor, the thermal conductor extending from within the cooling chamber to within the insect chamber.

In embodiments, the cooling chamber has a mutual wall with the insect chamber, the mutual wall comprising a thermal conductor.

In embodiments, the thermal conductor comprises aluminum.

Embodiments may comprise a controller. The controller may control the temperature around the insects by ventilating the insect chamber when the insect chamber temperature falls below a predetermined minimum value, and/or stopping the ventilating when the insect chamber temperature reaches a predetermined maximum value. The controller may use software or firmware or be hardwired and may conveniently be a programmable logic controller (PLC).

The controller may control the temperature around the insects by switching on heating elements when the insect chamber temperature falls below a predetermined minimum value and/or switching off the heating elements when the temperature exceeds a predetermined maximum value.

In embodiments, the source of passive cooling is dry ice, and the dry ice is vented to the outside to divert carbon dioxide away from the insects.

Embodiments may comprise one or more carousels, the or each carousel comprising a plurality of the insect compartments. The or each carousel may have its own release point, the insect compartments arriving one by one at the release point as the carousel rotates.

Alternatively, the insect compartments may be stationary, and the release point may rotate on the carousel.

In embodiments, the release point comprises an open floor, the insects falling through the floor as the release point is reached, or the release point comprises a closable opening, the closable opening configured to be open when an insect compartment is present to release the insects.

In embodiments, the carousel has a variable rotation rate.

In embodiments, the release point comprises a closable opening, the closable opening configured to be open when an insect compartment is present to release the insect compartment.

In embodiments, the insect compartment comprises a cavity built into a conveyance unit such as the above-mentioned carousel. However the conveyance unit could alternatively be a linear conveyor.

The insect compartment may comprise a cylinder.

Embodiments may comprise an actuator that applies a knock or vibration to an insect compartment at the release point to ensure effective insect release and shake out any insects that get clogged inside.

Embodiments may comprise a release chamber beneath the release point into which insects from the insect compartment are dropped prior to release.

Embodiments may comprise a heating unit in association with the release chamber to warm up the insects.

Embodiments may comprise a shutter at an outlet of the release chamber, the shutter configured to be opened following a predetermined time delay after the insects are dropped in from the heating container, the predetermined time delay being selected to give time to the heating chamber to heat the insects sufficiently to make them more active.

A second aspect of the present invention may relate to a drone carrying the insect distribution device as discussed herein.

A third aspect of the present invention may relate to a method for aerial release of insects, comprising:

loading the insects into a plurality of insect compartments;

loading the compartments onto a feeding system, the feeding system being configured to feed the plurality of compartments to a release point;

placing a passive cooling element in thermal contact with the feeding system or a chamber containing the feeding system;

loading the feeding system and the passive cooling element onto a drone;

controllably releasing the insects from the drone by feeding the insect compartments to the release point and releasing.

In embodiments, the insects are released at the release point.

Alternatively the insect containers are released at the release point.

The method may involve using the passive cooling element together with a warming procedure to keep the chamber containing the feed system within upper and lower bounds of a preset temperature. The warming procedure may comprise opening the chamber to outside air, operating fans or operating warming elements.

The method may comprise applying a vibration or a knock or puffing to ensure release of the insects.

The method may comprise varying a strength of the knock or a duration or strength of the vibrations or duration and velocity of puffing air.

According to a fourth aspect of the present invention there is provided an insect distribution device for carrying by drone to distribute insects from the air, the device comprising:

a source of passive cooling;

an insect chamber;

at least one release zone; wherein the source of passive cooling is in thermal contact with the insect chamber to keep the insects below a predetermined temperature, the predetermined temperature selected to keep the insects passive during storage, the device being configured to cause the insects to reach the release zone for aerial release.

The term "release zone" refers to a position which may be a single location or to an extended zone from which the insects are able to exit.

According to a fifth aspect of the present invention there is provided a method for aerial release of insects, comprising:

loading the insects into at least one insect chamber;

loading the chamber onto a feeding system, the feeding system being configured to feed the insects to a release zone;

placing a passive cooling element in thermal contact with the feeding system or a chamber containing the feeding system;

loading the feeding system and the passive cooling element onto a drone; and controllably releasing the insects from the drone by feeding the insects to the release zone.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the Drawings:

FIGS. 18 and 19 are two views of a carousel according to an alternative embodiment of the present invention;

FIGS. 24A to 24F are various views of an insect release chamber in which canisters are released with the insects inside according to a further embodiment of the present invention;

FIGS. 25A to 25D are further views of the insect release chamber of FIGS. 24A to 24D, showing details of the cooling and temperature regulation mechanism and the release mechanism;

FIG. 29 is a simplified side view of an embodiment of the present invention in which an intermediate chamber is placed between the cold chamber and the insect release chamber;

DESCRIPTION OF SPECIFIC EMBODIMENTS OF THE INVENTION

Figure 1:
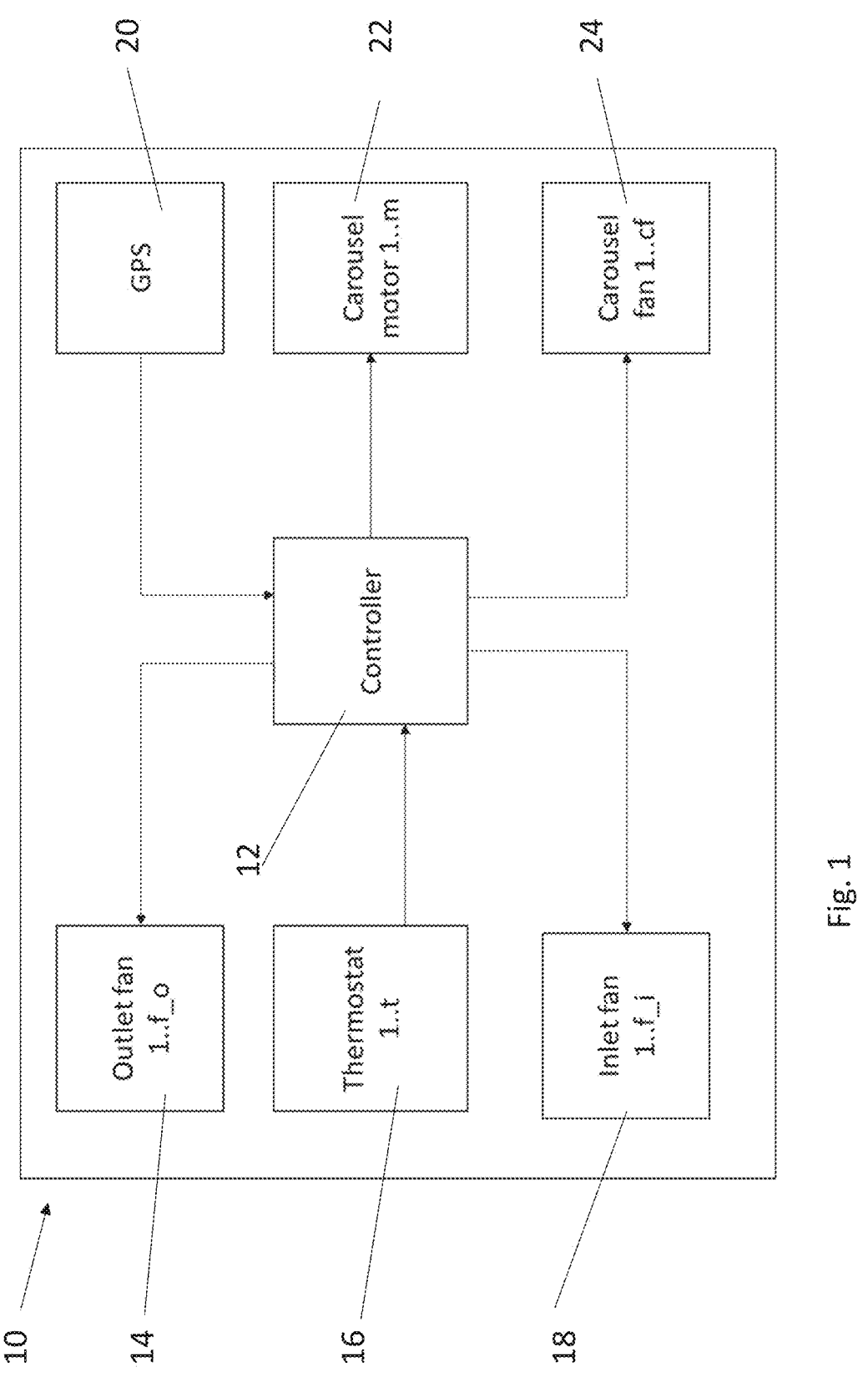
FIG. 1 is a simplified block diagram illustrating a controller and wiring for operating a controlled temperature storage and distribution system suitable for an aerial drone according to embodiments of the present invention.

As stated above, the present invention, in some embodiments thereof, relates to a system and method for automated cooling storage transport and release of beneficial insects and, more particularly, but not exclusively, to such a system for use with drones.

In order to minimize the volume of the storage compartment a drone carries, while still carrying a large number of insects and not causing them damage, the insects may be placed in an immobile state.

Immobilization of insects may be achieved using one or a combination of several techniques, including by lowering the surrounding temperature, or by sedating the insects using gas such as $CO_2$. Thus lowering the temperature may involve cooling the insects to around 5 degrees Celsius in the case of mosquitoes. It is noted that using $CO_2$ may damage the insects.

One embodiment provides a light-weight passive cooling unit, a storage compartment for the insects with its associated release mechanism, a frame for holding the storage compartment and a release mechanism.

One embodiment has a passive cooling unit which make use of dry ice as a cold source. The typical weight of the dry ice block or blocks used in the solution may be less than 4 Kg to the levels of dozens or hundreds of grams, but even so providing many hours of cooling before they evaporate.

Dry ice temperature is well below 0 (zero) degrees Celsius, and is thus harmful for living insects.

Such low temperatures may also be harmful to other objects which can benefit from drone delivery while being kept cold (e.g. blood packs, vaccine doses, frozen foods).

Dry ice is additionally harmful as it evaporates $CO_2$ which may be harmful to living organism depending on the dose.

Embodiments include a first chamber of dry ice as the cold source and a second chamber containing the target material to be cooled, and a thermal heat transfer unit (a unit with good thermal conductivity) located in between them allowing the cold source to cool the heat transfer unit which would then cool the second chamber with the target material in it, while not transferring any harmful gas into the secondary chamber.

Extracting the gas may preferably be achieved by having a small ventilation hole at the first chamber directing the evaporated $CO_2$ gas from the dry ice away from the secondary chamber, and directly out from the first chamber, say into the open air. Guidance of the gas out may also be achieved my having multiple holes, or having a permeable surface or a duct.

An inlet fan may be provided for the insect chamber, preferably mounted on one of its frame walls, to bring air in from the outside to control the temperature inside the chamber when it gets too cold.

Another fan may serve as an outlet fan, and blow air outside from within the insect chamber, also to control the temperature inside the chamber by extraction of cold air to the outside. Triggering of the fans is in accordance with the temperature within the insect chamber and a thermostat or any other means may be used to measure temperature.

According to the present embodiments, the number of insects released or the number of compartments that are emptied may be associated with numbers of wild insects are in the environment. The numbers may differ for different geographical release locations, so that the drone or drones may be provided with a plan for releasing different numbers of insects in different places. That is to say, the mechanism of the present embodiments may accurately release predetermined dosages of insects at different release point to accord with available data. Specifically the embodiments release the insects on the basis of compartments or containers and this allows for specifying of how many compartments are to be released at each location.

Embodiments may thus provide an insect distribution device to be carried by drone to distribute insects from the air, comprises a source of passive cooling; an insect chamber; one or more insect containers in said insect chamber; and a release point. The source of passive cooling is in thermal contact with the insect chamber to keep the insect container below a predetermined temperature to keep said insects passive during storage. The device is designed to feed the insect containers in turn to the release point for aerial release. At the release point, an opening in the floor, or opening of a shutter or the like in the floor may cause the insects to drop out. This may be assisted by giving the container a knock with an actuator. The actuator may be located either at the side of the container or above, and knocking of the container may cause release of the insects in the release position. The knocking may cause a vibration-like operation on the container to deal with clogged material. Alternatively, a suitably located vibration motor may vibrate the container to support the release of the insects. Alternatively a fan may blow air down the container to assist with release or a plunger may be used to push the insects out.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a simplified block diagram of hardware forming a device for storage and release of insects according to an embodiment of the present invention. FIG. 1 illustrates a device 10 comprising a controller 12 which provides commands for operation of fans in order to maintain a temperature in a space in which the insects are stored at a required target level, for example 4-6 degrees Celsius may be a suitable temperature for a given series of mosquito. The controller may be based on software, firmware or hardware and may be programmable logic controller (PLC).

The controller 12 is connected to the outlet fans 14, a thermostat 16 which reads the target chamber temperature, which may be one reading in one location or multiple readings for multiple locations, and to inlet fans 18. It also communicates with a GPS or other navigation component 20 receiving information as per its location in order to operate the carousel motors 22 and the carousel fans 24 which are part of the insect release system, to release the insects where needed, as will be discussed in greater detail below.

Figure 2A:
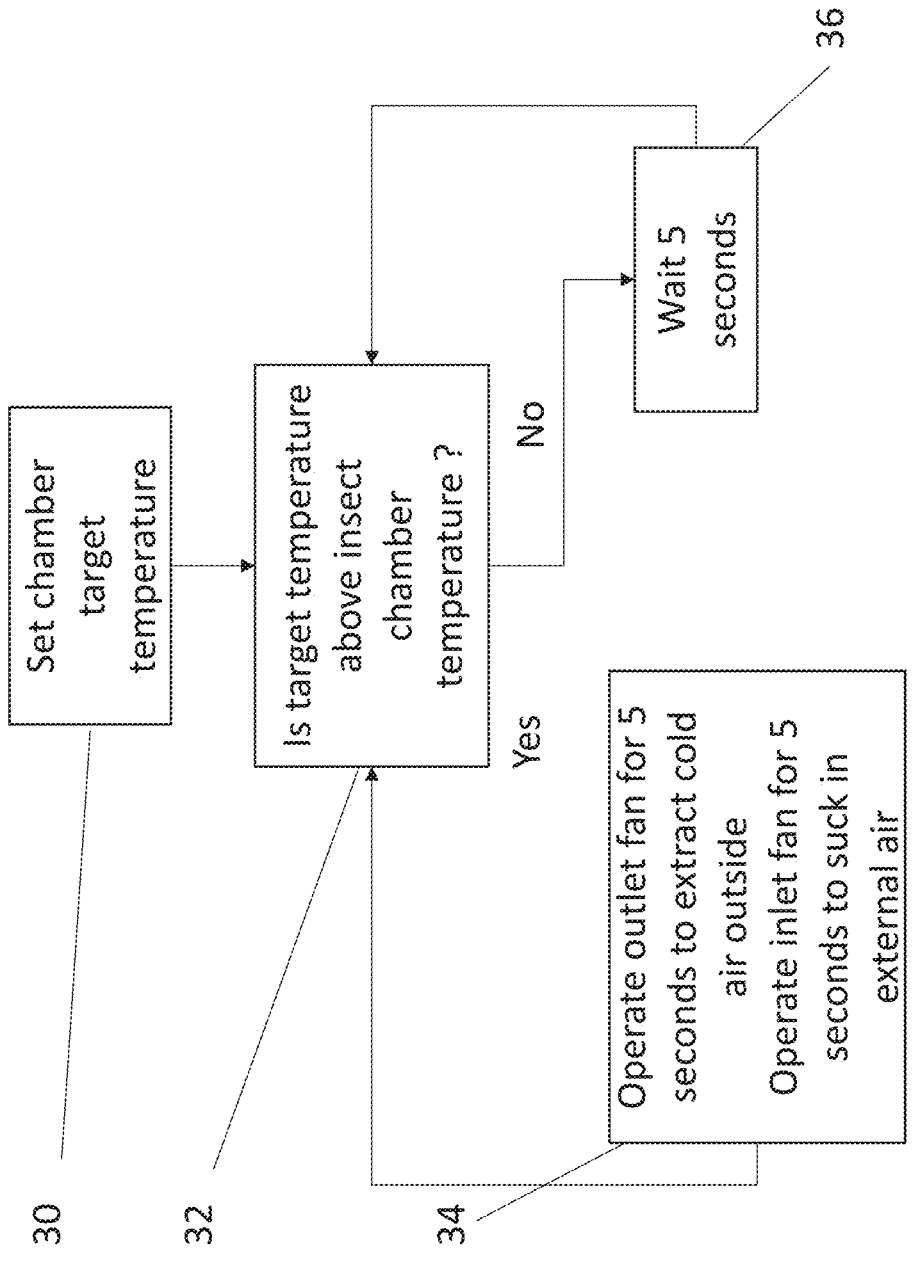
FIGS. 2A to 2C are three simplified flow charts showing control sequences for the controller of FIG. 1.
Figure 2B:
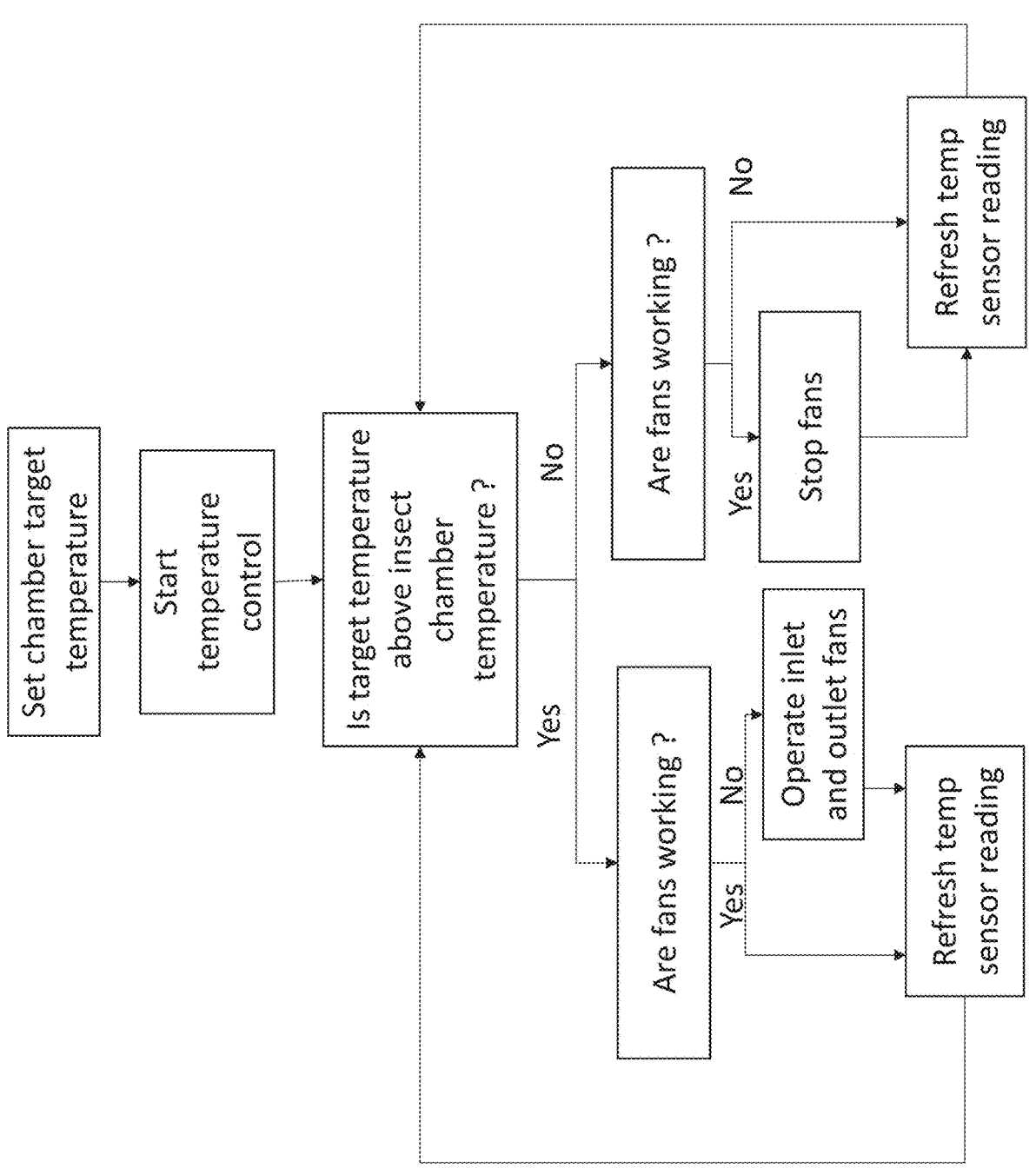
Figure 2C:
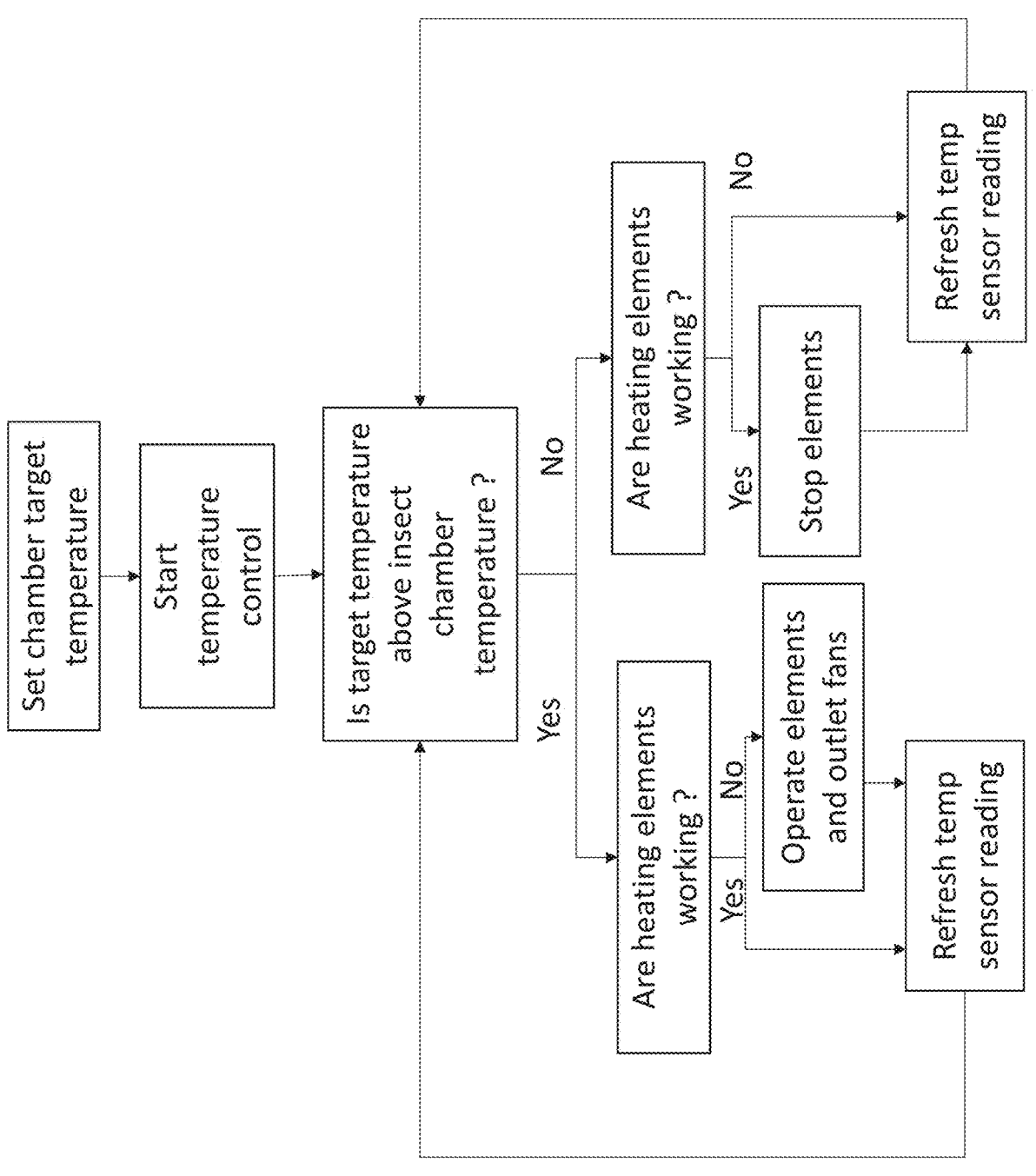

Reference is now made to FIGS. 2A to 2C, which are three simplified exemplary flow chart showing how the temperature may be maintained by the controller 12. The controller initially sets a target temperature—30. The actual temperature is measured and checked for being too low, compared to the target—32. If the temperature is indeed too low then the outlet and inlet fans are operated for five seconds to replace cold air with warmer external air—34. If no discrepancy is noted then the controller simply waits five seconds—36. At the end of the five seconds, flow returns to box 32 and the controller checks the temperature again.

Alternative logic flows may be applied, such as sensing the rate the temperature is increasing or decreasing instead or in addition to sensing the current temperature. In an embodiment an outlet fan may be dispensed with and one or more inlet fans may bring in warmer air from the outside. Passive outlets may be one or more fixed holes or even a permeable surface or the outlet(s) may include a shutter which is opened and closed by the controller 12. In an embodiment, the inlet fan may be dispensed with and a passive inlet or permeable surface or shutter may be used with an active outlet fan.

In use, if the temperature as measured is above the target the system simply waits as the cooling system, if operating properly, will reach the target temperature. Once the temperature is below the target, the flow as above opens the air inlet in the various ways described. It will be appreciated that other time delays may be used and the five seconds is merely an example.

In an embodiment, once the fan is on it may remain on until the temperature has increased above the target to an upper set temperature which is above the target temperature, and then the fans may close, allowing the temperature to start dropping again.

A possible procedure may be as follows. The controller 12 determines that the chamber temp is too low and starts warming as before. A subsequent check shows the temperature to be too high, and stops the fans so that the chamber starts cooling all over again.

Suitable upper and lower target temperatures around the target temperatures may be discretionary parameters for the system.

FIG. 2B differs from FIG. 2A in that if the temperature is too low—the yes branch—then inlet and outlet fans are operated to bring in warm air. If the temperature is too high—the no branch—then the fans are stopped so as to allow the cold source to do its work.

FIG. 2C differs from FIG. 2B in that heating elements are switched on if the insect chamber is too cold.

A dry ice chamber may be provided in association with the insect chamber holding the insects, as will be explained in greater detail below, and may include an exit hole or holes for evacuation of gas to guide the gas outside of and away from the chamber. The dry ice chamber may also include an outlet fan which may actively push and propel air outside, being controlled by the controller. Also the dry ice chamber may include a duct along which the gas passes away from the dry ice chamber.

Figure 3:
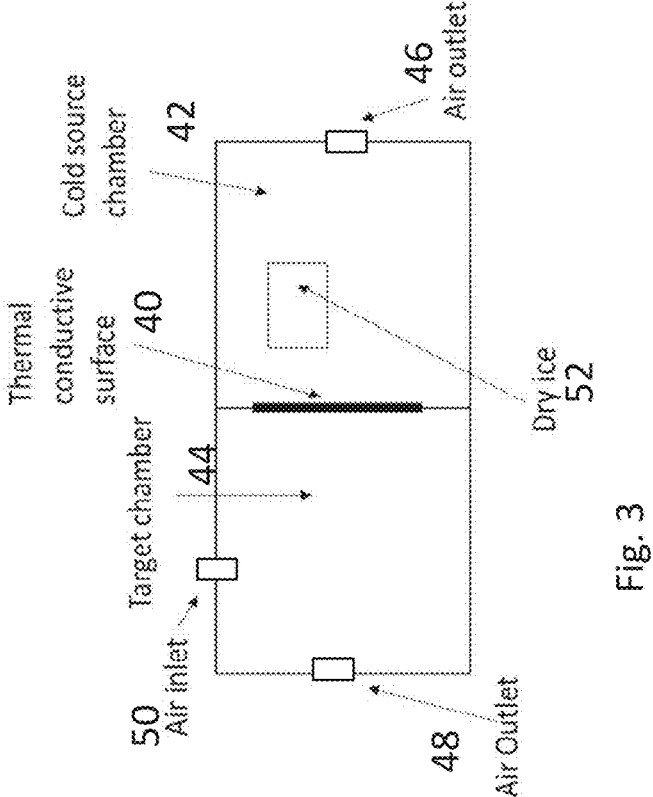
FIG. 3 is a simplified plan view of a cold chamber thermally linked to an insect chamber according to embodiments of the present invention.

Referring now to FIG. 3, a heat transfer surface 40 may be part of the mutual wall, between dry ice or cold source chamber 42, and target insect chamber 44 and thus transferring the cold from the cold chamber to the target chamber through the mutual wall. The two chambers are thus isolated from each other, preventing evaporated gas from reaching the target chamber. Each chamber 42, 44, has an air outlet 46, 48 and the target chamber 44 has an air inlet 50. The air outlet 48 of the insect chamber 44 may also serve as an outlet for the insects to exit from when being distributed.

Dry ice 52 may be placed and mounted directly on or in proximity to heat transfer surface 40. In an embodiment, the dry ice is located within the cold source chamber 42, and the heat transfer surface 40 is also located within the cold source chamber but does not touch the dry ice. Rather the heat transfer surface 40 absorbs the cold temperature within the chamber and transfers the cold to the other side of the heat transfer surface, which is a surface of the target insect-holding chamber 44. The heat transfer surface may thus be the mutual wall between the cold source chamber and the target chamber, meaning its first side is part of the target chamber wall and its second side is part of the cold chamber wall.

Figure 4:
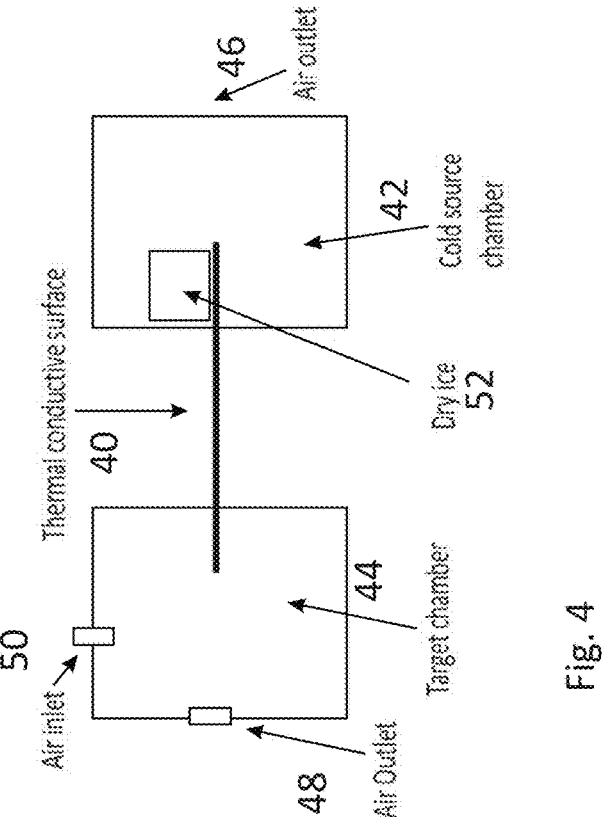
FIG. 4 is a simplified plan view of an alternative embodiment in which a cold chamber is thermally linked to an insect chamber.

Referring now to FIG. 4, an embodiment is shown in which the two chambers do not share a mutual wall. Parts that are the same as in previous figures are given the same reference numerals and are not described again except as needed for an understanding of the present embodiment. In the embodiment of FIG. 4, the heat transfer surface 40 may not be part of the mutual wall, but rather extends along the dry ice (cold source) chamber 42, and then continues onwards, penetrating and extending along and within the target insect chamber 44 and thus transferring the cold from the cold chamber along the internal volume of the target chamber. The two chambers are thus isolated from each other, preventing evaporated gas from reaching the target chamber, as seen in the following drawing. Each chamber 42, 44, has an air outlet 46, 48 and the target chamber 44 has an air inlet 50. The air outlet 48 of the insect chamber 44 may also serve as an outlet for the insects to exit from when being distributed.

Accordingly, the two chambers do not touch each other, and the thermal conductive surface may transfer the cold temperature from the cold source to the target chamber. The Target chamber 44 may have a single opening serving both as inlet and outlet with the ability to control the fan to switch between suction and blowing.

Figure 5:
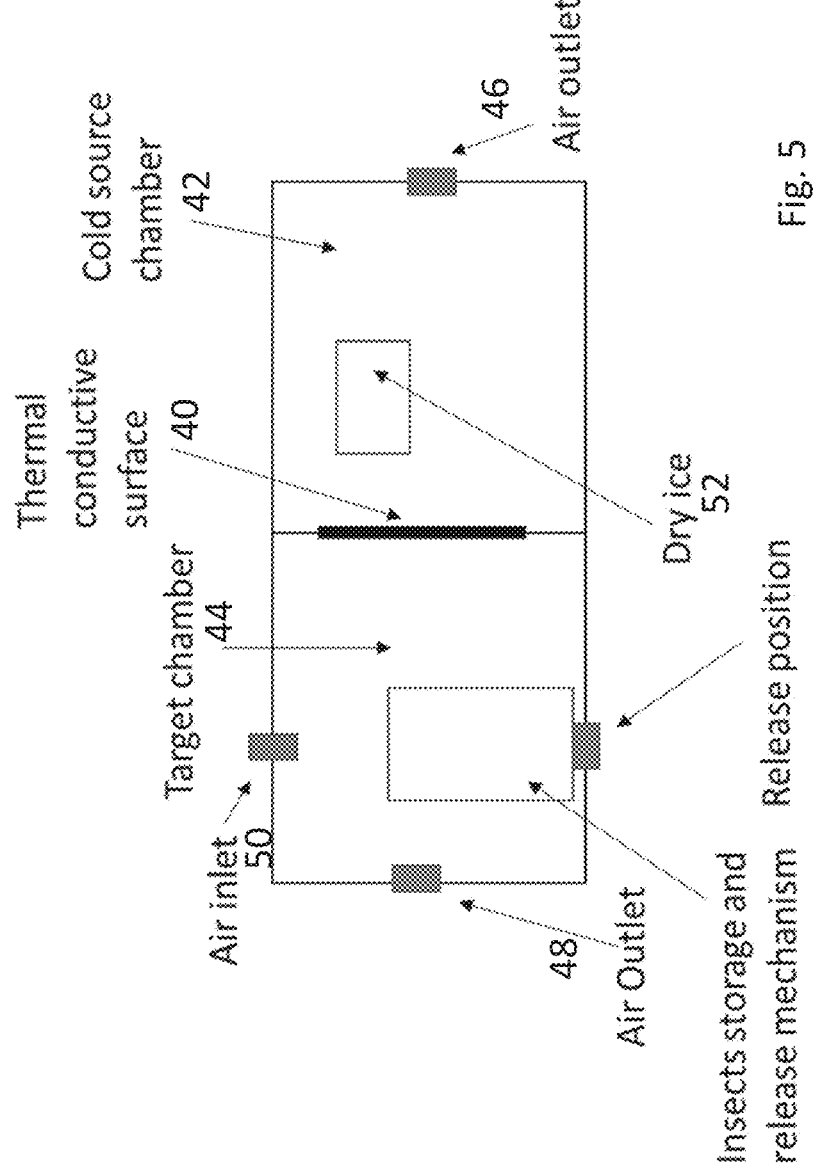
FIG. 5 is a simplified plan view of a cold chamber thermally linked to an insect chamber according to a further embodiment of the present invention.

Reference is now made to FIG. 5, which shows a modification of the embodiment of FIG. 3 including an insect release mechanism. Parts that are the same as in previous figures are given the same reference numerals and are not described again except as needed for an understanding of the present embodiment. An insect release mechanism 54 provides insects from the chamber 44 to an insect release position 56. Using the release mechanism 54, insects may be controllably released from the insect storage chamber 44.

Figure 6:
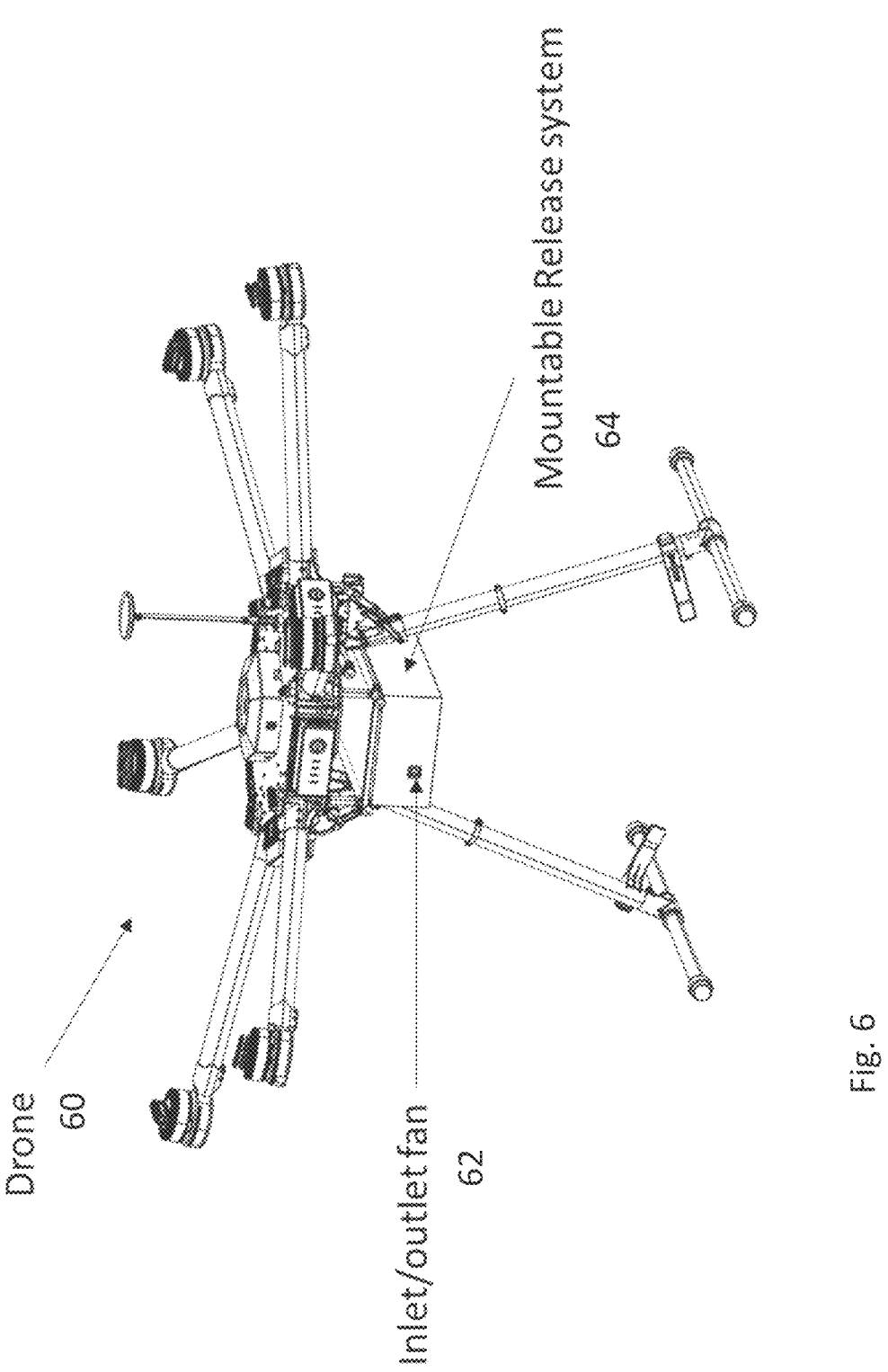
FIG. 6 is a simplified diagram illustrating an aerial drone on which is mounted a controlled temperature storage and distribution system according to embodiments of the present invention.

Reference is now made to FIG. 6, which is a simplified schematic diagram showing a drone 60 that mounts both the dry ice chamber and the insect storage chamber, the insect storage chamber including inlet or outlet or combined inlet and outlet fans 62, all in a mountable release system 64.

Figure 7A:
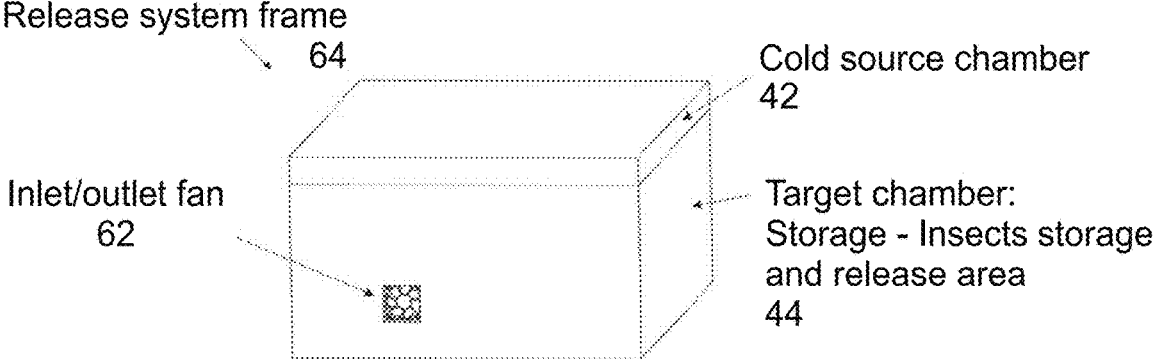
FIGS. 7A and 7B are simplified views of two alternative versions of the controlled temperature storage and distribution system of FIG. 6.

FIG. 7A shows the mountable release system 64 of FIG. 6 in greater detail. Parts that are the same as in previous figures are given the same reference numerals and are not described again except as needed for an understanding of the present embodiment. The mountable release system 64 holds within a housing or frame the cold source or dry ice chamber 42 and the target insect chamber 44. Fan 62 may be an inlet or outlet fan or both as discussed hereinabove.

While the main embodiments herein discuss the storage of insects within the target chamber 44, the chamber may store other types of materials required storage at a controlled temperature, being lower than the external temperature and further requiring controlled release and or transportation.

Figure 7B:
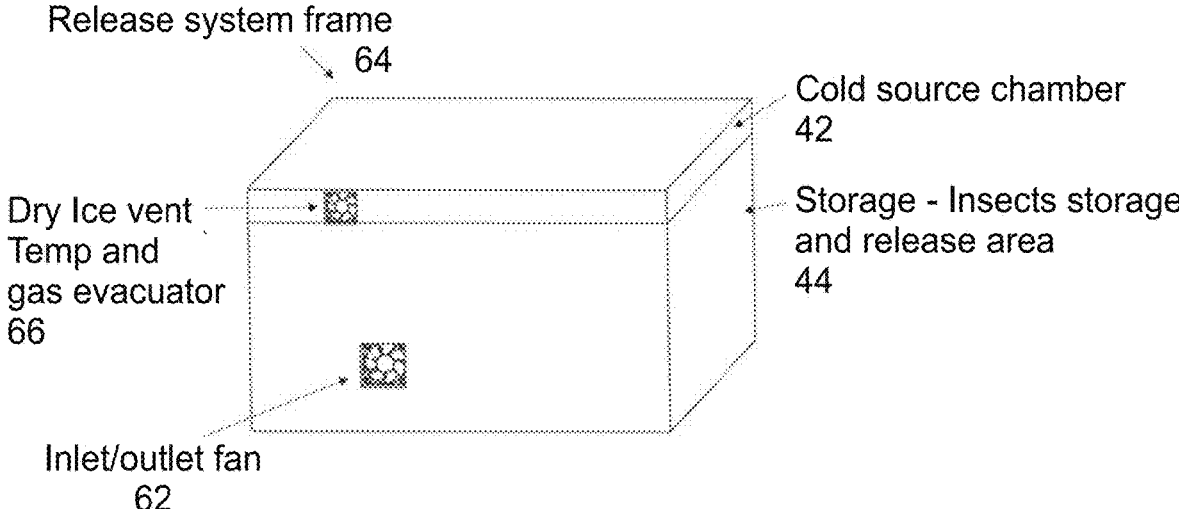

Reference is now made to FIG. 7B, which illustrates a variant of the release system of FIG. 7A having active ventilation 66 associated with the cold source chamber 42, actively extracting cold air and gas. Parts that are the same as in FIG. 7A are given the same reference numerals and are not described again except as needed for an understanding of the present embodiment.

Figures 8, 9:
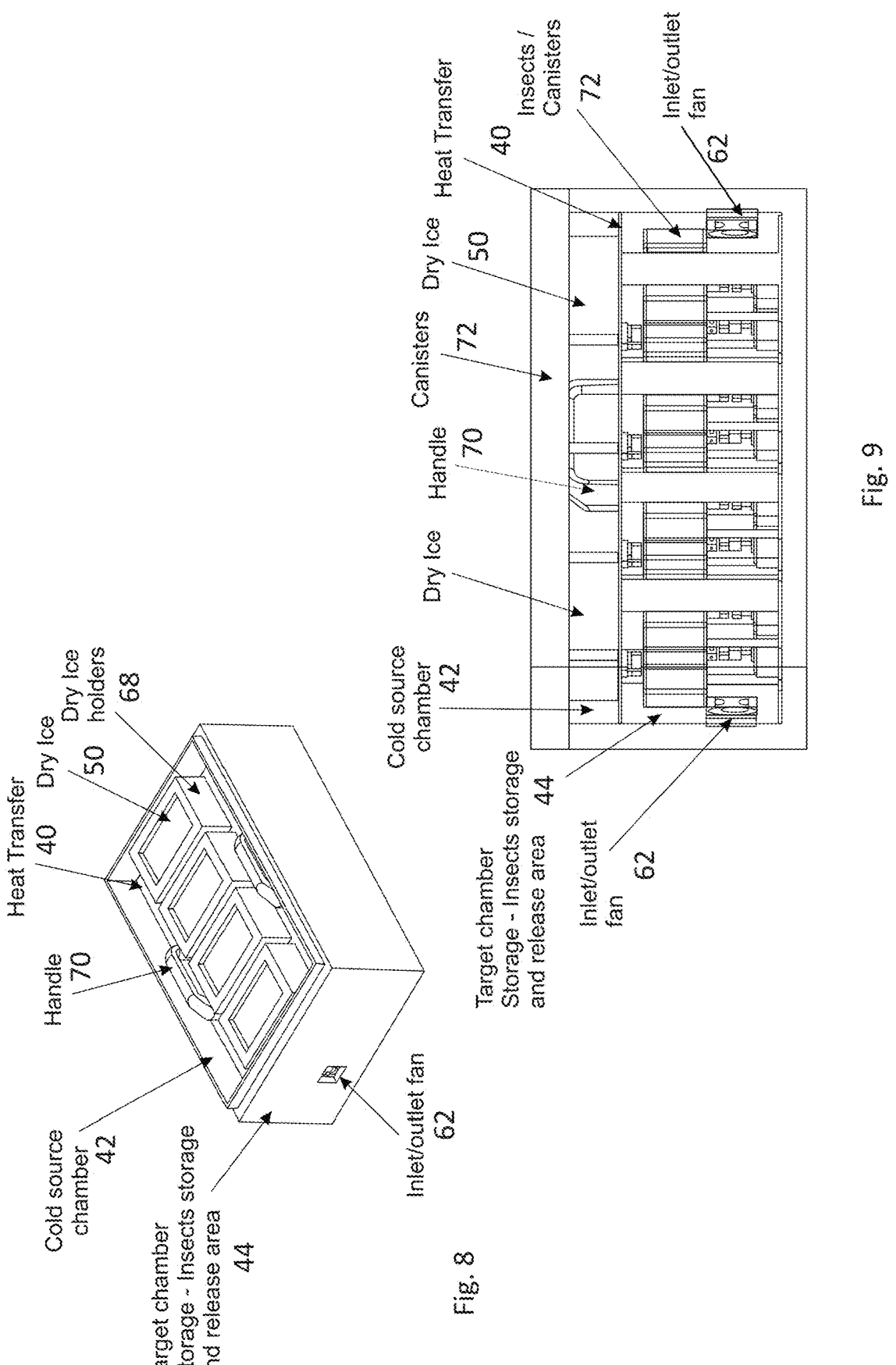
FIGS. 8 and 9 are perspective and side cutaway views respectively of the controlled temperature storage and distribution system of FIG. 6.

Reference is now made to FIG. 8, which is a simplified schematic diagram showing the inside of the mountable release system within the housing as viewed from the side of the cold source chamber 42. Dry ice 50 is placed within dry ice holders 68, mounted on top of a heat transfer surface 40, made for example of aluminum which is a material selected for good thermal conductivity. Handles 70 may be provided to lift the dry ice units to reach the target chamber 44. The dry ice is thus located within the cold source chamber 42.

In an embodiment, the entire frame holding the cold source chamber and the target chamber is designed for controlled temperature transportation, and there is no release mechanism. Such a system may be used to rapidly transfer highly perishable foodstuffs, for example, such a system may allow for drone-based transportation of products requiring refrigeration, for example medical supplies, such as blood, medicines, vaccines, and organs, frozen foods, and drone delivery may be used for freshly caught fish from a fishing port or even directly from a fishing boat.

In the following there is described an embodiment having a release system. Such a release system is associated with the target chamber 44 and may include release holes and release positions.

Reference is now made to FIG. 9, which is a cutaway side view of the target chamber 44 and the cold source chamber 44. Parts that are the same as in FIGS. 7A.B and/or 8 are given the same reference numerals and are not described again except as needed for an understanding of the present embodiment. Below the heat transfer surface, is located the area where the objects to be kept cold are to be found. In an embodiment the objects are insects, and in embodiments the insects are adult mosquitoes or adult fruit flies or other adult flies.

The target chamber 44 may include insect storage units in the form of cannisters 72 which include or are connected to release mechanisms for release of the insects.

Figure 10A:
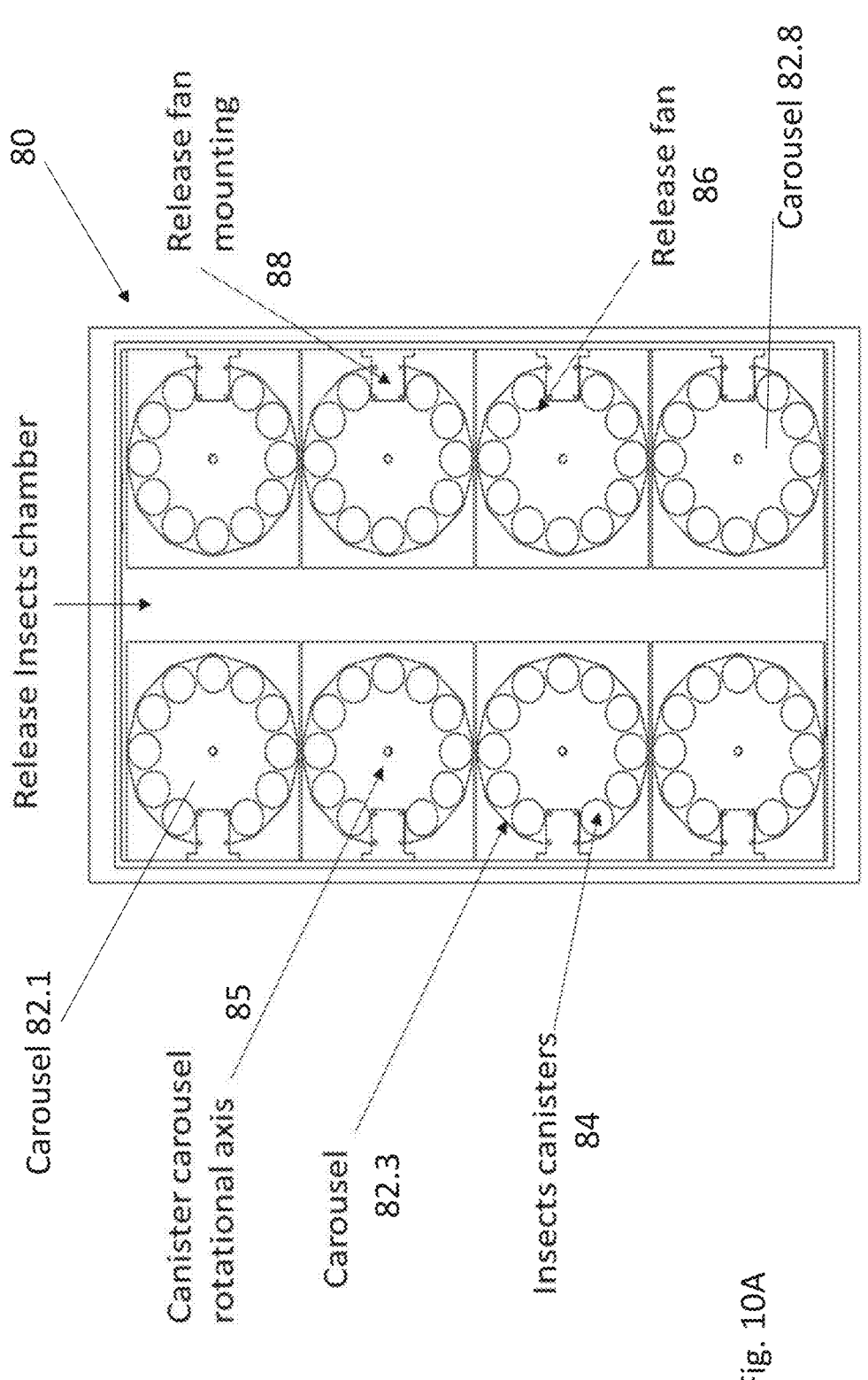
FIGS. 10A to 10C are simplified plan and perspective views of an insect chamber equipped with multiple carousels for storing and releasing insects according to embodiments of the present invention.
Figure 10B:
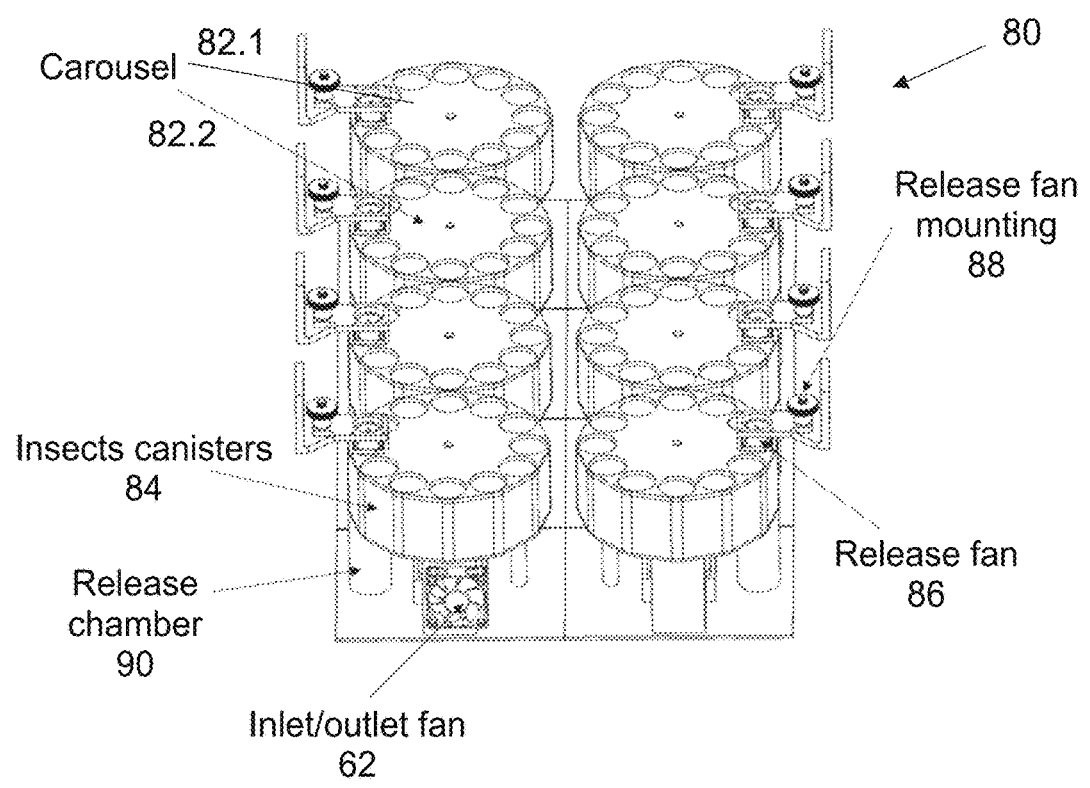
Figure 10C:
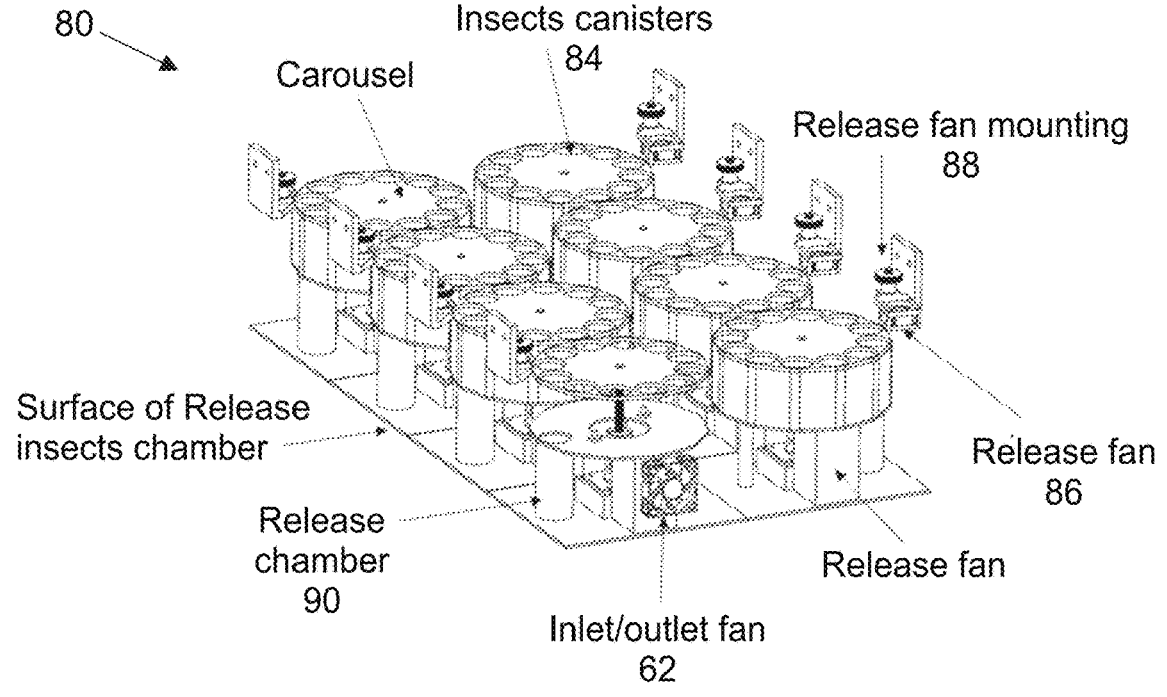

Reference is now made to FIGS. 10A-10C which are views from above and from perspectives, which illustrate an insect release system 80 according to an embodiment of the present invention, which release mechanism may be mounted within target insect chamber 44.

The insect release system is based on a carousel design. Carousels 82.1 . . . 82.8 each hold a series of canisters 84 within their circumferences. The insects are held in the internal volumes of the canisters 84 within the body of the respective carousel.

The carousel rotates around axis 85 to convey the canisters in turn towards a release position where a release fan 86, mounted on a release fan mounting 88, is ready to empty the canister.

As the carousel rotates, each canister in turn arrives at the release point, where there is an opening or a cavity or a pathway or similar means to allow insects to move through, and the insects fall out into the air, for example propelled by the fan 86. In embodiments the release opening may be a release chamber 90. A door, or a shutter, gate, or similar, may be provided at the surface of the canister or a release chamber if used, and in one embodiment there is provided a heating chamber to revive the insects to be more active prior to release from the drone.

As shown in FIGS. 10B and 10C, the release fans are adjusted before use to be above the canister that is currently at the release position.

Figure 11:
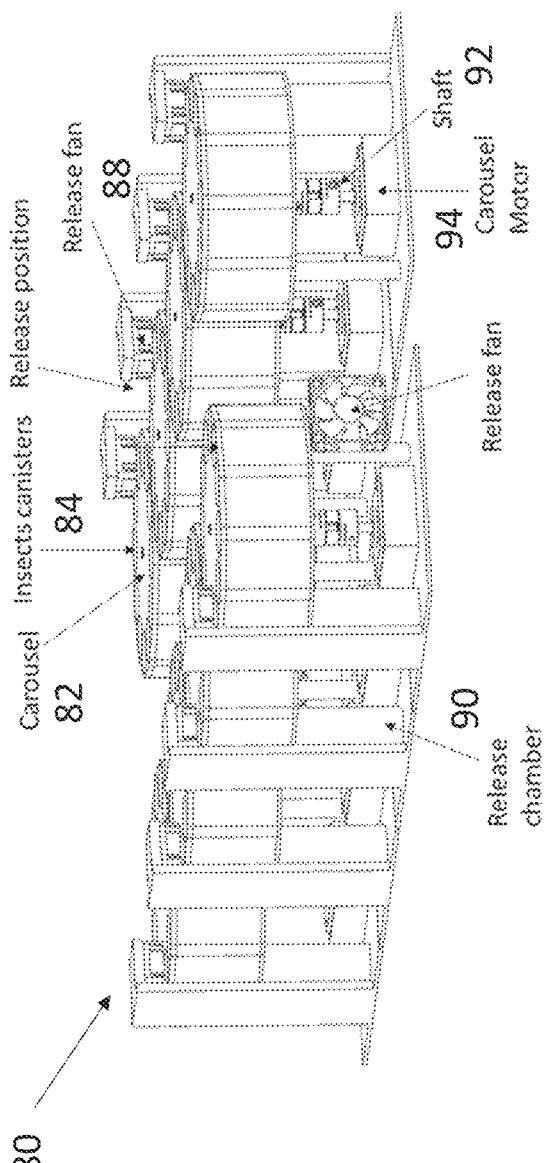
FIG. 11 is a lower side perspective view of the insect chamber of FIGS. 10A to 10C showing carousel motors and drive shafts.

FIG. 11 is a side view of the carousel release mechanism 80. As the insects are being conveyed to the release position, an insect propelling mechanism may push or puff them outside or, as discussed, a knocking or vibrating mechanism may knock or vibrate the carousel or the canister to ensure that all of the insects fall out. In an embodiment, the propulsion mechanism is the release fan 86 located at the release position being an air pressure source to puff the insects out as shown in FIGS. 10A to 10C. Other possible conveying mechanisms can be for example the usage of a piston which is located at the release point above the canister hole. Upon activation, a piston enters into the canister and pushes the insects out from the other side as it propagates along the inside of the canister. Such a piston may be pneumatic, electric, hydraulic or other. The speed of the piston may be fixed or variable. Such a piston may be controlled by controller 12, and replaces the fan in FIGS. 10A to 10C.

The insects may be released from release chamber 90 through a release hole. In embodiments a release chamber is not used and the insects fall or are ejected or puffed away from the canisters directly through a release hole.

Each carousel is mounted on a shaft 92 and the shaft is rotated by a carousel motor 94.

Figures 12A, 12B:
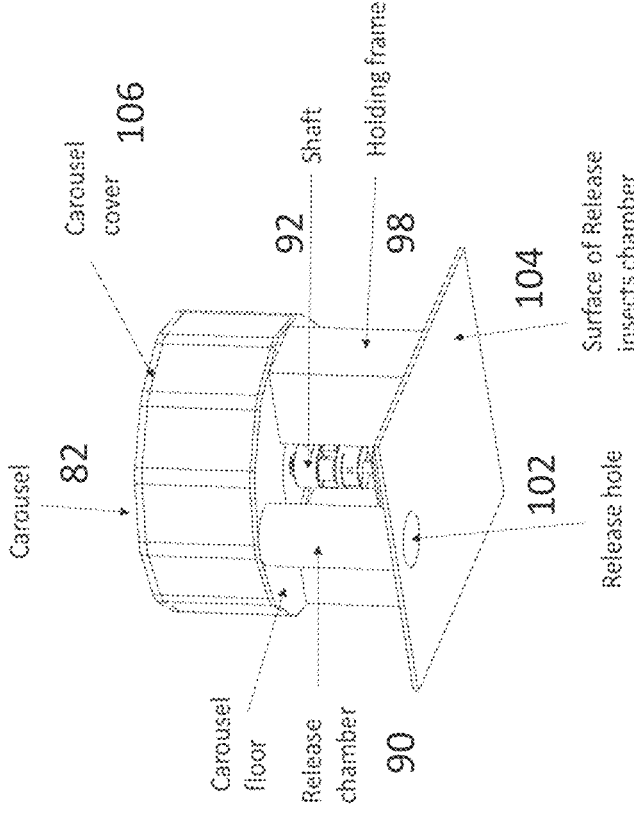
FIGS. 12A and 12B are perspective views of a carousel and an associated insect release point according to embodiments of the present invention.

FIGS. 12A and 12B show individual carousels 82 with canisters 84 at the release point. Each carousel may be mounted to the insect chamber 44 via a holding frame 98. The canister is thus located between release fan 86 and release chamber 90. FIG. 12A shows three release holes 100. FIG. 12B shows a variant in which the base of the release chamber 90 forms a release hole 102 in the surface 104 of the insect chamber 84.

In an embodiment the canister diameter is 3 cm, and its height is 5 cm. In order to avoid compaction of the insects, specifically adult immobilized mosquitoes, it is preferred that the canister or cavity holding the insects is loaded with adult insects up to 6 cm in depth, and preferably over a 3 cm diameter. Other sizes may apply, for example lcm diameter and 5 cm height, or with larger diameter. Release fan wind speed velocity may preferably be in the range of 3-7 meter per second, while other velocities may be applied, depending on the fragility of the insect. Mosquitoes are notoriously fragile while flies are much resilient.

In an embodiment, the carousel includes a carousel cover 106, preferably including a net or a mesh surface which may partially or fully cover any openings at the locations of the canisters where the insects are located.

Figures 13, 14, 15:
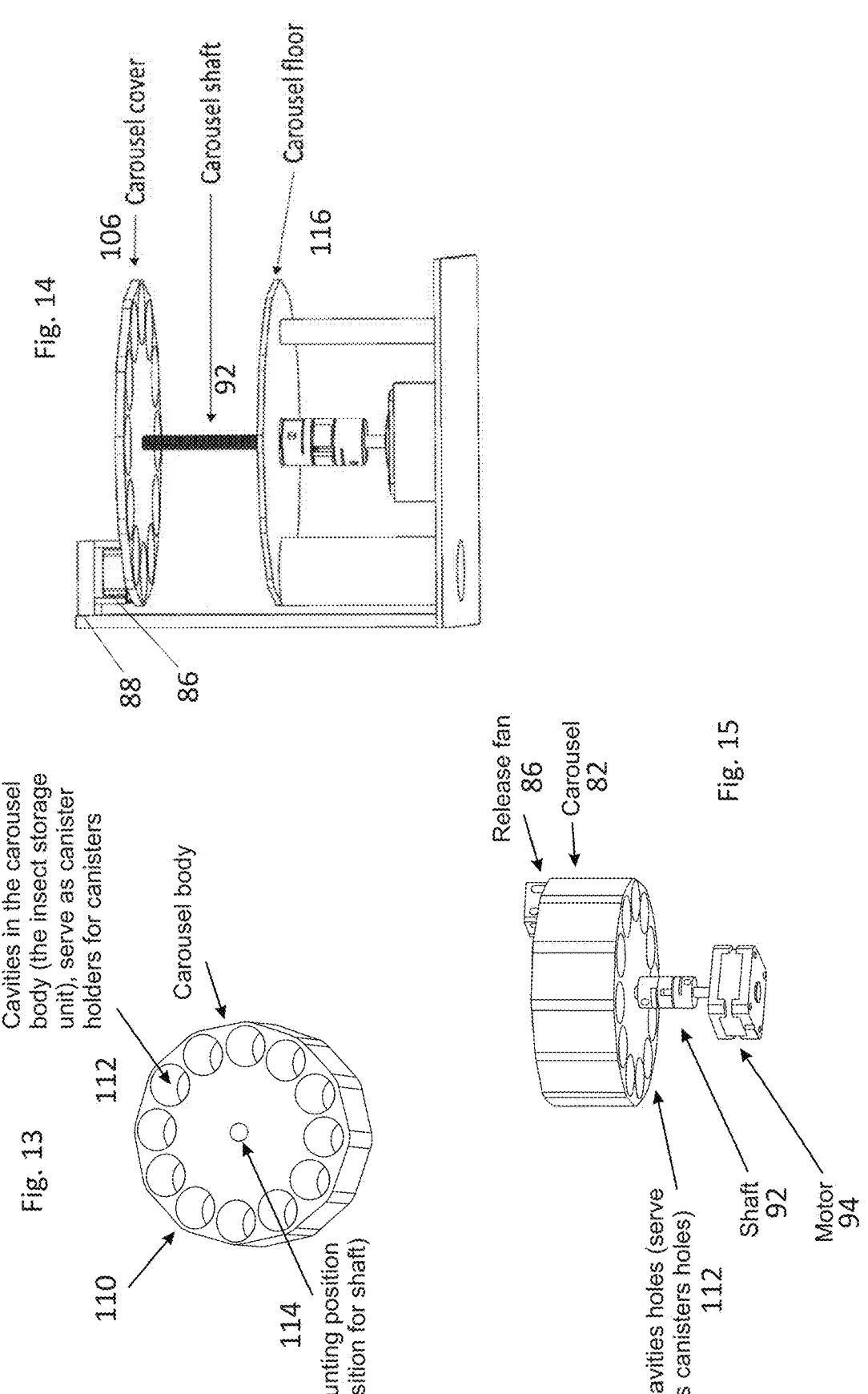
FIG. 13 is a simplified perspective view of a carousel using cavities to store the insects, either directly or via canisters, according to embodiments of the present invention.
FIG. 14 is a side cutaway view of a carousel according to embodiments of the present invention.
FIG. 15 is a simplified lower side perspective view of a carousel according to embodiments of the present invention.

Reference is now made to FIG. 13, which shows a carousel 110 comprising empty volumes or cavities 112 within the carousel body which can store the insects. That is to say, instead of having canisters, the carousel comprises cavities 112 which contain the insects. The carousel body rotates around central axis 114 as before however the internal volumes 112 hold the insects in place of canisters.

The carousel in the various above examples have a circular shape and as it rotates, the insects resting within the canisters or cavities and on the carousel floor are rotated against the carousel floor.

The carousel floor may itself rotate in one embodiment and bring the release hole to the canister, enabling insects from a different canister each time to exit by falling or ejecting or blowing through the release hole.

FIG. 14 is a cutaway side drawing showing the carousel cover 106, the shaft 92 which goes through the carousel body (not shown) and the carousel floor 116.

Reference is now made to FIG. 15, which shows the carousel body. Release fan 86 sits above the release point. Cavity holes 112 either hold insects themselves or accept canisters, and motor 94 rotates shaft 92 which rotates the carousel.

The carousel floor may provide a surface with at least one hole or pathway through which the insects may be released. In other embodiments there is no carousel floor as each canister may have its own opening door as will be explained hereinbelow and the canisters are conveyed without rotating against a floor.

Figures 16, 17A, 17B, 17C:
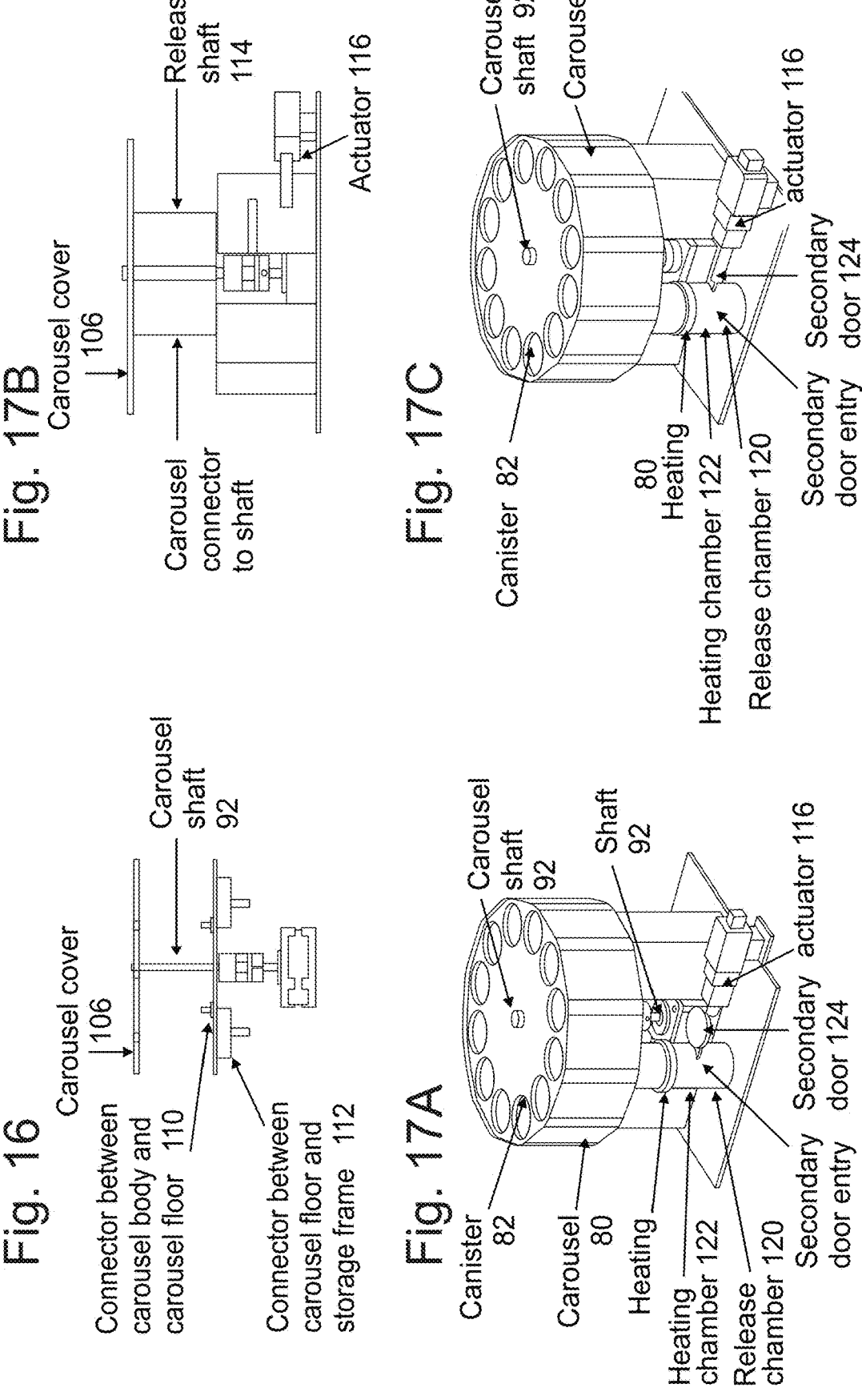
FIG. 16 is a side view of a carousel frame showing connectors according to embodiments of the present invention.
FIGS. 17A to 17C are three views of a carousel according to embodiments of the present invention and showing a release mechanism for releasing the insects.

In an embodiment, the carousel body holds the insects directly within the carousel body cavities, without any box, or canister mounted in the cavity, in order to ease the loading process of insects into the carousel cavities. Referring to FIG. 16, the body may be removed to fill the cavities with insects. A release device such as a connector 110 between the carousel body and floor or a connector 112 between the carousel floor and storage frame can be for example a magnet or set of magnets. The magnet may be connected to the carousel body, and the carousel floor may be made of a material that is attracted to the carousel body. The magnet may then allow rotation against the magnet. When lifting the body out for loading of insects, the body may then come out together with the carousel floor, allowing insects to be poured into the cavities. The floor below each cavity may support storage of the insects within each cavity.

The carousel body together with the carousel floor may be attached using a magnet to the storage frame.

The canisters may include their own floor. An advantage of having canisters is that the insects move together with the floor and not against it as with the option of the carousel body in which insects rotate with the body against the floor, increasing the risk of causing damage to some of the mosquitoes. On the other hand an advantage of having the carousel body with insects loaded directly into the cavities yields a simpler design, fewer components and faster loading.

Reference is now made to FIGS. 17A to 17C which are perspective and side view respectively of a carousel according to a further embodiment of the present invention. Canisters are released via a release shaft 114. The mechanism is operated by actuator 116. The cavities are the locations or volumes to store insects on the carousel and may be loaded directly with insects, or canisters may be loaded into the cavities.

As shown, the insects are released through a release chamber 120 which may include a heating device that may increase the temperature in the heating chamber 122, to awaken the insects prior to their release.

A secondary door 124 may be used to retain the insects within the heating chamber until the door is opened and the insects may be extracted by falling or ejecting.

The door holding the insects may be actuated by actuator 112 moving a plate in and out. Thus in FIG. 17C, the actuator pushes the secondary door element 124 into the secondary door entry into the release chamber to close. FIG. 17A illustrates the open state, in which the element 124 is out of the release chamber letting the insects fall. A door for an intermediate chamber serving as a heating chamber may be implemented in many ways such as rotating door (instead of moving back and forth), shutter, electric, pneumatic or other.

Reference is now made to FIG. 18, which shows an alternative construction in which the carousel 130 holding the insects may be divided into storage cells 132 in other shapes, as opposed to the cylindrical cavities shown above, and the insects may be directly poured onto the carousel cells. The carousel floor 134 may be fixed and the release position may simply have a missing segment of floor serving as release hole 136. A release path may be defined by guide walls 138 and heating element 140 is optional to heat the insects before falling down. A release hatch 142 may be provided to delay release of the insects until they are fully revived by the heater. A cold chamber may be provided (not shown). The insects may be mosquitoes, fruit flies, or any other insect or material required cooling and release as discussed above.

Figure 19:
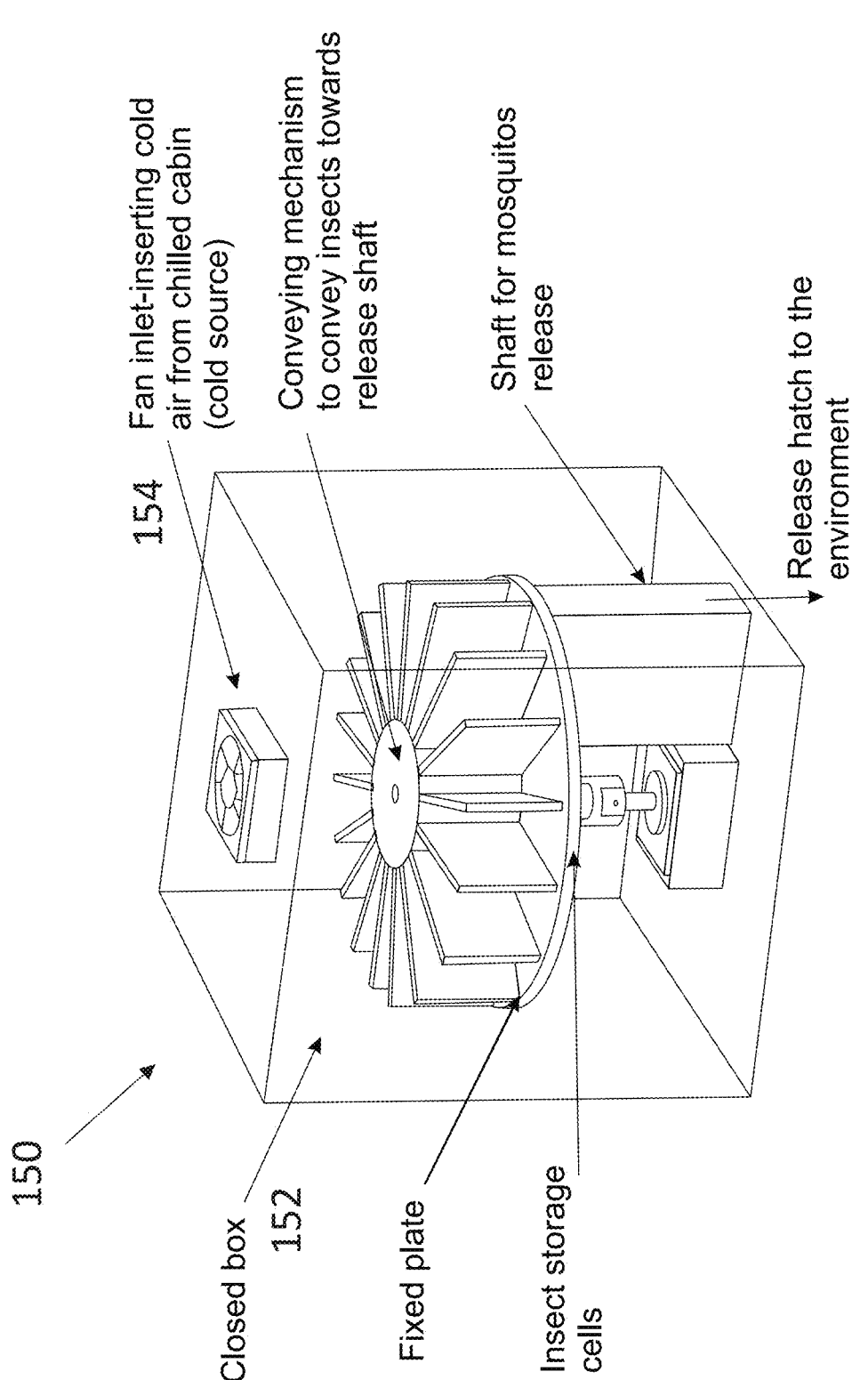

Reference is now made to FIG. 19, which shows a carousel insect storage and release device 150 according to the embodiment of FIG. 18 inside a frame or a box 152, the frame or box holding the mechanism together. A fan 154 is located above the box to introduce cold air, and may also prevent air coming in from the outside into the box.

Figure 20:
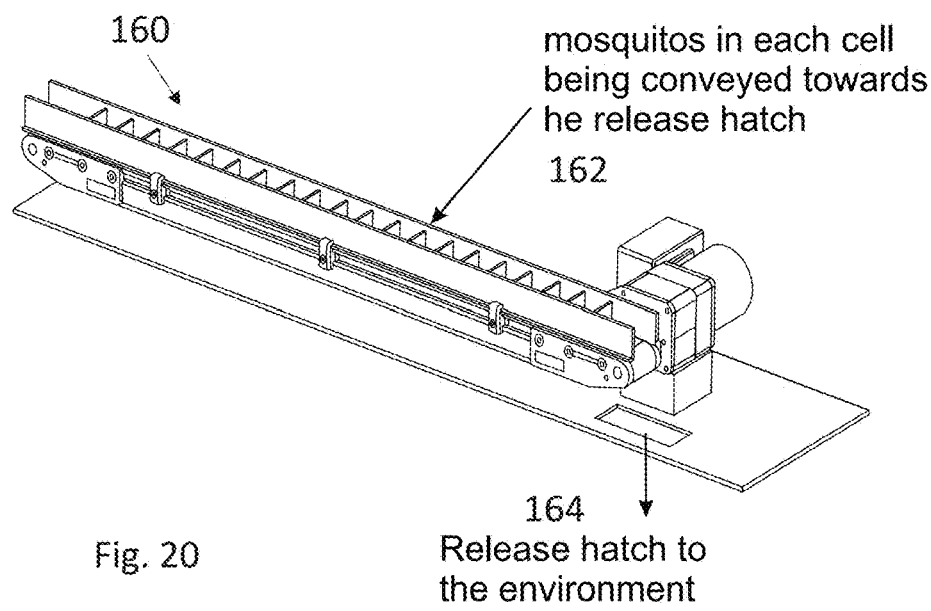
FIG. 20 is a simplified diagram showing a linear conveyer according to an alternative embodiment of the present invention.

Reference is now made to FIG. 20, which illustrates a linear conveyor 160, in place of a carousel, to convey insects towards the release position, or release hatch. Such a linear system may be implemented together with the controlled cooling of the present embodiments. In the linear conveyor 160 are cells 162 which continuously convey the insects toward the release position. At the release position, the insects are dropped or ejected through release hatch 164.

Figure 21:
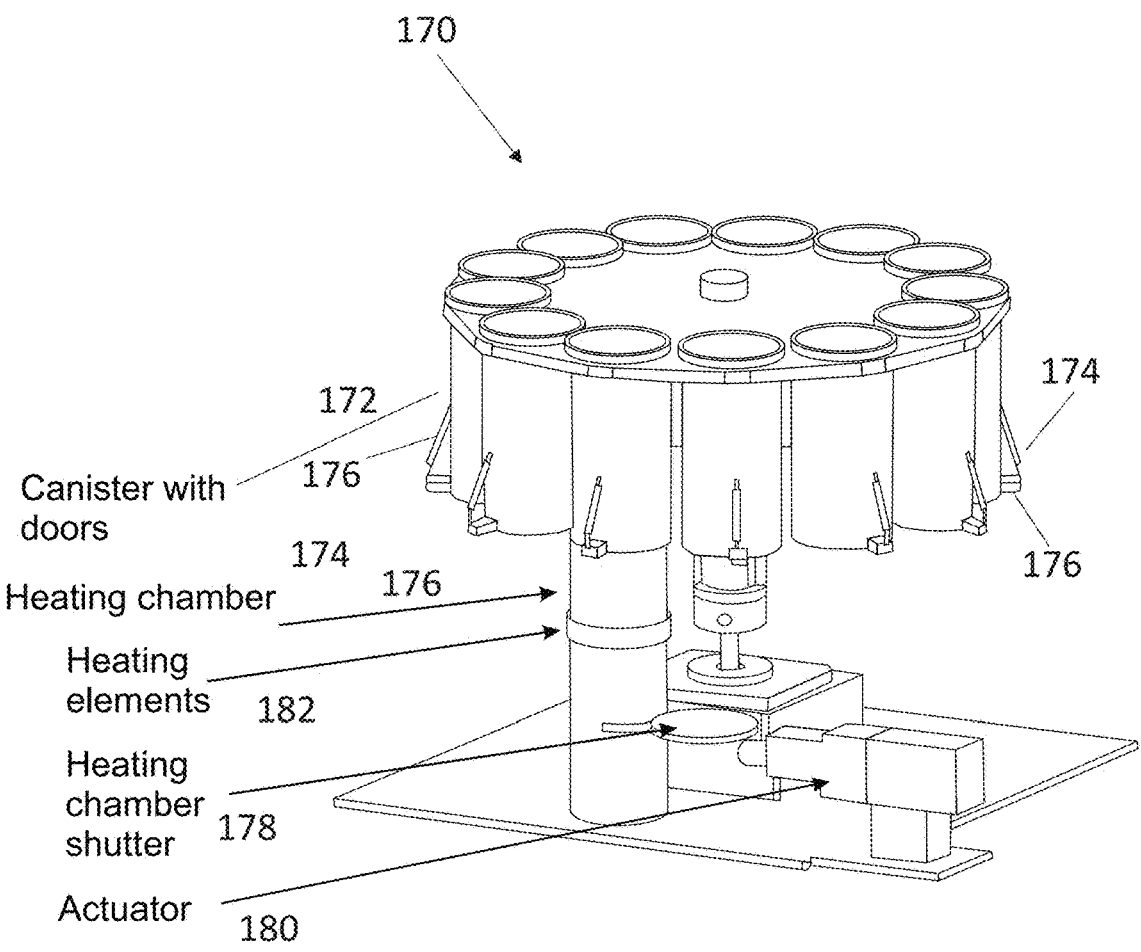
FIG. 21 is a simplified diagram showing a cutaway view of a carousel according to the present embodiments and illustrating an opening mechanism for releasing the insects.

Reference is now made to FIG. 21, which again shows a carousel 170 with canisters 172. Each of the canisters 172 has its own opening and its own release door 174 which can be opened using an opening mechanism that opens doors at a release position.

A spring 176 holds the door 174 normally closed, and a latch (not depicted) at the release position may cause the spring to open the door. As the latch returns to its original position the door closes again, placing the insects in heating chamber 176. The heating chamber detains the insects while they are warmed and revived and then they are released to the outside by opening shutter 178. There are various ways of opening shutter 178, say via actuator 180, and the operation may typically be controlled by controller 12 after the canister has been in the release position and the insects have had time to revive. Hence the opening mechanism is in sync with the release operation. In use, the insects are stored in the canisters 172 and each canister has a door 174, instead of having a single floor for all the canisters. When the door opens the insects fall out. Optional heating chamber 176 comprising a heating element 182. The insects may fall or be expelled from the canister into the heating chamber when the canister door 174 is opened. In the heating chamber they are warmed and revived and then released into the environment via shutter 178, which is in this example the heating chamber shutter being pushed in and out by the actuator 180. The shutter 178 may be moved linearly, rotationally, and may be electric, pneumatic, based on magnets, and the like.

Figure 22:
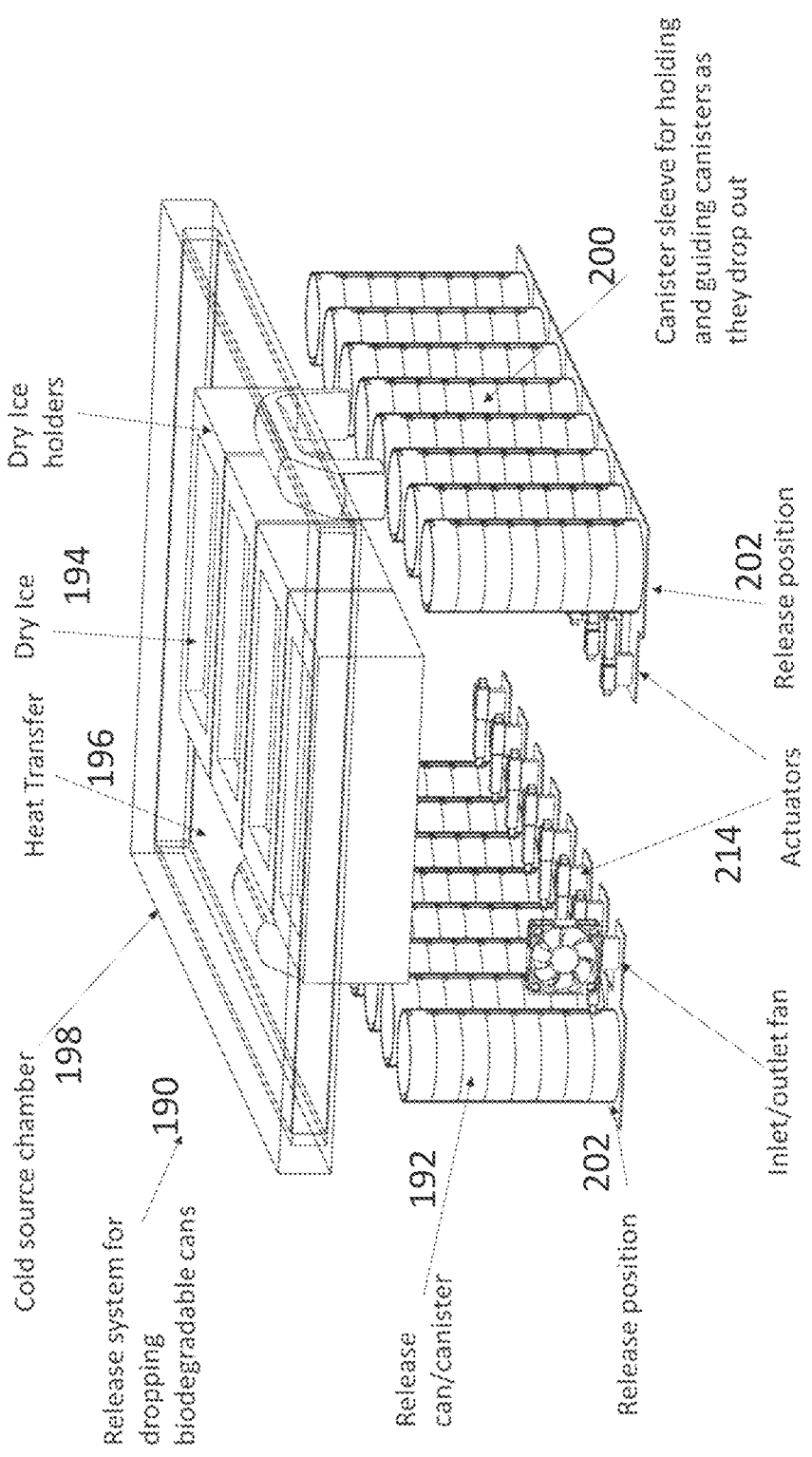
FIG. 22 is a simplified exploded view of an insect release chamber according to a further embodiment of the present invention.

Reference is now made to FIG. 22, which is a simplified diagram showing a release system 190 according to the present embodiments that includes dropping of the canisters out from the drone, instead of merely releasing the insects. The release mechanism stores and then drops release canisters, and the canisters are dropped either in parallel or one after the other in a controlled sequence.

The canisters may be biodegradable.

The insects storage and release canisters 192 are placed within the insect chamber, with a separation from the cold source 194 using the heating transfer surface 196. The cold source 194 is in a cold chamber 198 and may be dry ice as was explained above. A temperature control method and system may be as described above and the insects are stored in canisters that are dropped. A conveying mechanism may convey the canister downwards along a canister sleeve 200 to release position 202 where there is a shutter and the shutters open to drop the canisters. A release position is located under each release can group. Canisters release mechanism. Actuators 204 may control the drop of the next canister in the queue. After dropping one canister, the next canister moves into position to be dropped.

Release holes, or a release exit or ejection opening, or ejecting section are closed in the image. Shutter openings may be implemented by many ways well known in the literature, such as rotational shutters, linear movable shutters, the shutters may be electric, pneumatic, or based on magnets as in previous embodiments.

Figure 23:
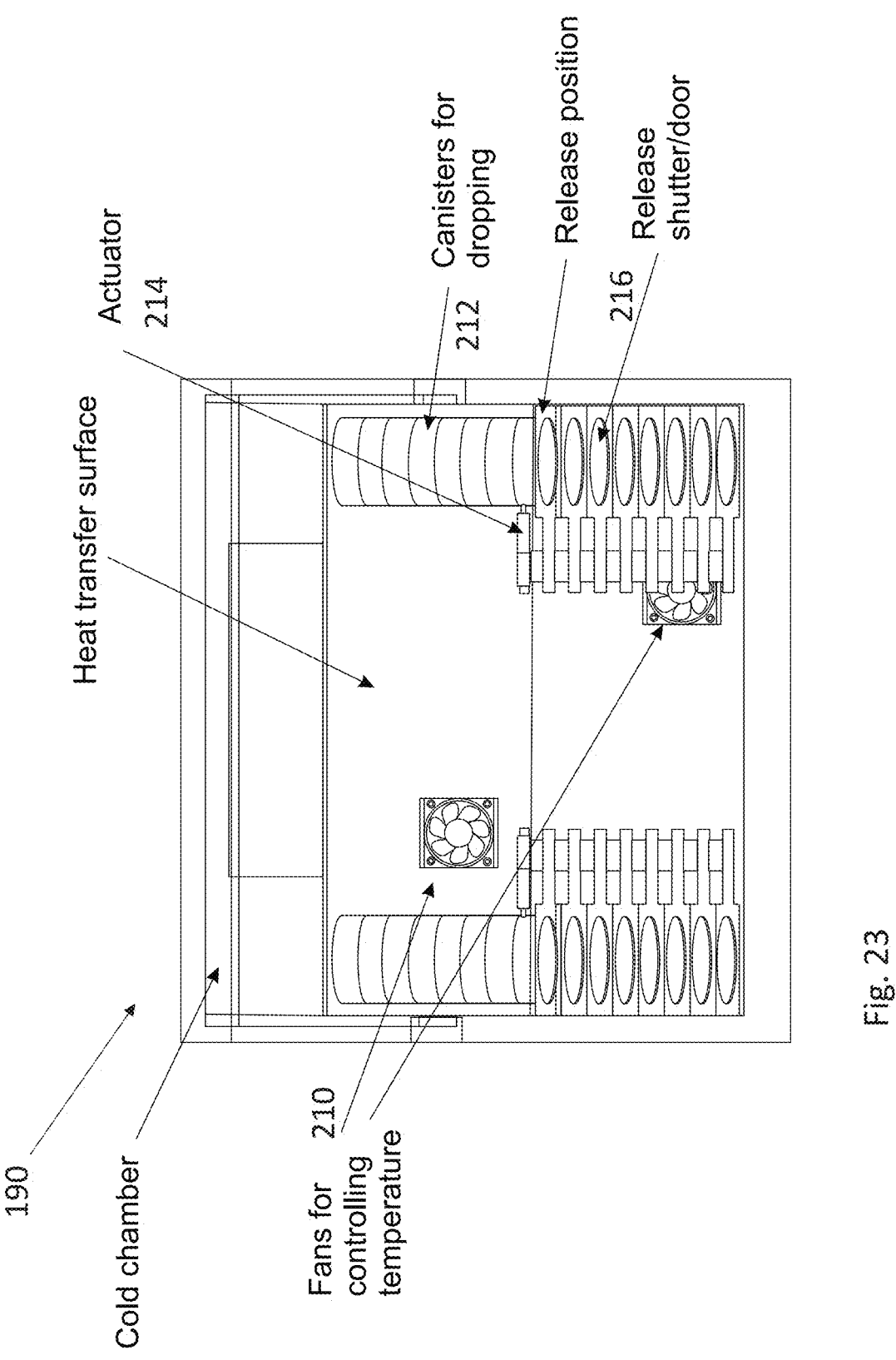
FIG. 23 is a side cutaway view of an insect release chamber according to embodiments of the present invention and showing a further release mechanism.

Reference is now made to FIG. 23, which is a view from the side of the release apparatus 190 of FIG. 22. Two fans 210 are located in the area of the target insect chamber. One fan pulls in air from the outside into the chamber and the other pushes air out. There may be more than one fan for suction and or blowing out, and their location may be varied within the target chamber, say on different sides of the target chamber). Variations may include an inlet fan only or an outlet fan only, as in the embodiments discussed above.

As shown in FIG. 23, there is a single column 212 of canisters, being mounted one on top of the other. An actuator 214 may prevent the group of canisters from falling down.

There is an exit door 216 which allows the first canister in the queue to fall.

The queue of canisters may be mounted within a canister sleeve 200 to support the cans as they propagate one after the other towards the release position.

The queue of release canisters may also be moved towards the release position via a motorized mechanism, and be guided to the release position on a rail or other guiding means. Alternatively, for simplicity and reduced weight of the drone payload, the group of canisters may fall simply using gravity, and may be stopped and released each time by syncing between a barrier and a release door.

Figure 24A:
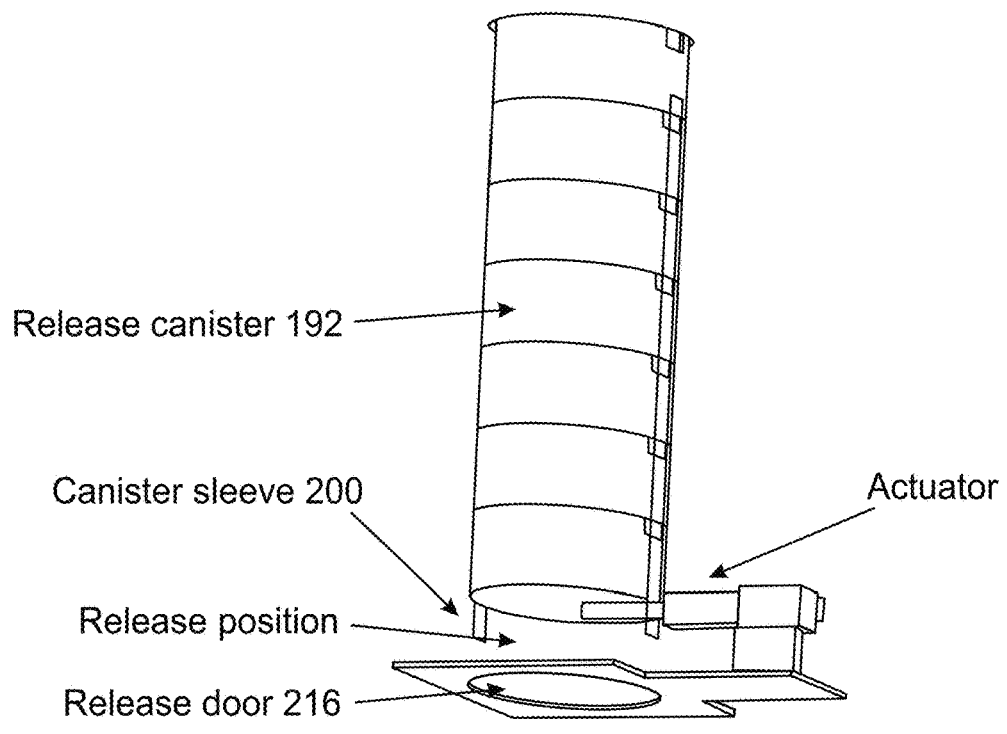
Figure 24B:
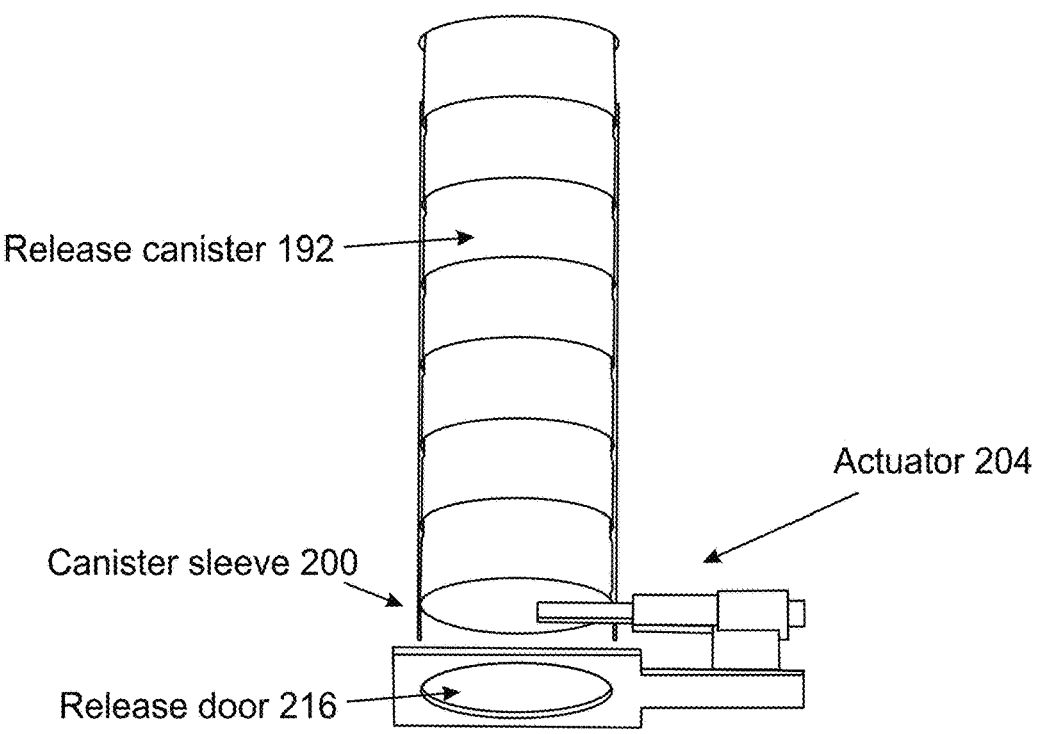

Referring to FIGS. 24A and 24B, the release door is open and there is an opening at the release position. Actuator 204 holds the canisters and opens the release doors to release the canisters one by one.

FIGS. 24C, 24D, 24E, and 24F show the release door in the closed position. The release canister which is next in line to be extracted is at the release position, and the barrier implemented by the actuator is in place, preventing the other release canisters from falling down once the door is opened.

Reference is now made to FIGS. 25A-25D, which are an upper perspective view, a top view, a side perspective view and a side cutaway view respectively, which show the canister release apparatus of FIG. 22. Fan 218 is located above or in proximity to the release sleeve 200. The fan may suck cold air from the cold source to cool the insects within the release canisters inside the release sleeve 200. The canisters are in a vertical pile, and are released one by one by actuator 204 into release sleeve 200 from where they fall out.

The present embodiments may provide an apparatus to use dry ice as a cold source for keeping materials in a controlled temperature in a storage and release compartment. The apparatus comprises dry ice as a source of cold air, a chamber holding the materials comprising at least one sides of the chamber made of material with high thermal conductivity to provide heat transfer between the dry ice and the insect chamber, a fan to extract air from the chamber and a fan to pull in external air into the chamber, thereby to control the internal temperature within the chamber.

Materials to be stored can range from live organism like mosquitoes, fruit flies and other insects, to dead insects which are required to be transported under cold conditions to other materials and objects which require storage and transport under cold conditions such as blood packages, vaccines, and even frozen food and beverages.

The temperature required may be below zero degrees Celsius or above the zero degree Celsius typically up to the temperature of the surrounding environment. A typical temperature for frozen food is −18 degrees Celsius, but say vaccines may require even colder temperatures.

An apparatus to use dry ice as a cold source for keeping materials in a controlled temperature in a storage and release compartment may use dry ice as a source of cold air. A chamber holding the insects may comprise at least one side of the chamber made of material with high thermal conductivity to provide heat transfer between the dry ice located outside of the insect chamber and the insect chamber. A fan may extract air from the chamber and a further fan may suck external air into the chamber to control the internal temperature within the chamber.

As an alternative to two fans, a single fan may switch between two modes extracting air from the chamber to the outside and sucking external air from the outside into the chamber, thereby to control the internal temperature within the chamber.

As a further alternative a single fan may suck in external air into the chamber, thereby to control the internal temperature within the chamber.

In an embodiment, the two chambers may be associated with a high conductivity surface supporting the transfer of cold temperature from the cold source chamber towards the insects chamber.

Embodiments may include a conveying mechanism and at least one canister for holding immobilized insects, the conveying mechanism able to convey the insects or the canisters holding the insects towards a release position, where a release mechanism releases the insects.

In embodiments, the dry ice may be located within the same chamber where the insects are located, and the evaporated gas is then guided away to prevent harmful effects on the insects. The temperature may be being controlled by letting in air from the outside. Alternatively, a fan may pull in external air into the chamber, to control the internal temperature within the chamber.

In any of the above embodiments, a conveying mechanism may convey the insects towards a release position, thereby to support the controlled release of immobilized insects.

In other examples, the heat transfer surface, may be a surface that extends between the inside of a cold chamber, including being in direct contact with dry ice, and the internal side of a target chamber where insects or other material required to be cooled are located). The cold is thus directed into the target chamber, and not necessarily by a mutual surface between the target chamber and a cold chamber. Insects may be provided in the target chamber and are kept dormant for storage purposes by the cold temperatures.

Insects may be held in an insect chamber where one wall is a thermally conductive wall. The insect chamber may have at least one fan. Dry ice positioned in close proximity to the thermally conductive wall may transfer cold across the wall and the fan or fans may expel cold air from within the chamber and/or suck air from the outside into the insect chamber, to control the temperature within the insect chamber.

The present embodiments may thus control the temperature within an insect chamber, and may include an insect release mechanism, which conveys or propels the insects towards a release position within the insect chamber, and allows the insects to fall by gravity into the open air. The device may be mounted on a drone to provide aerial release of insects.

Figure 26:
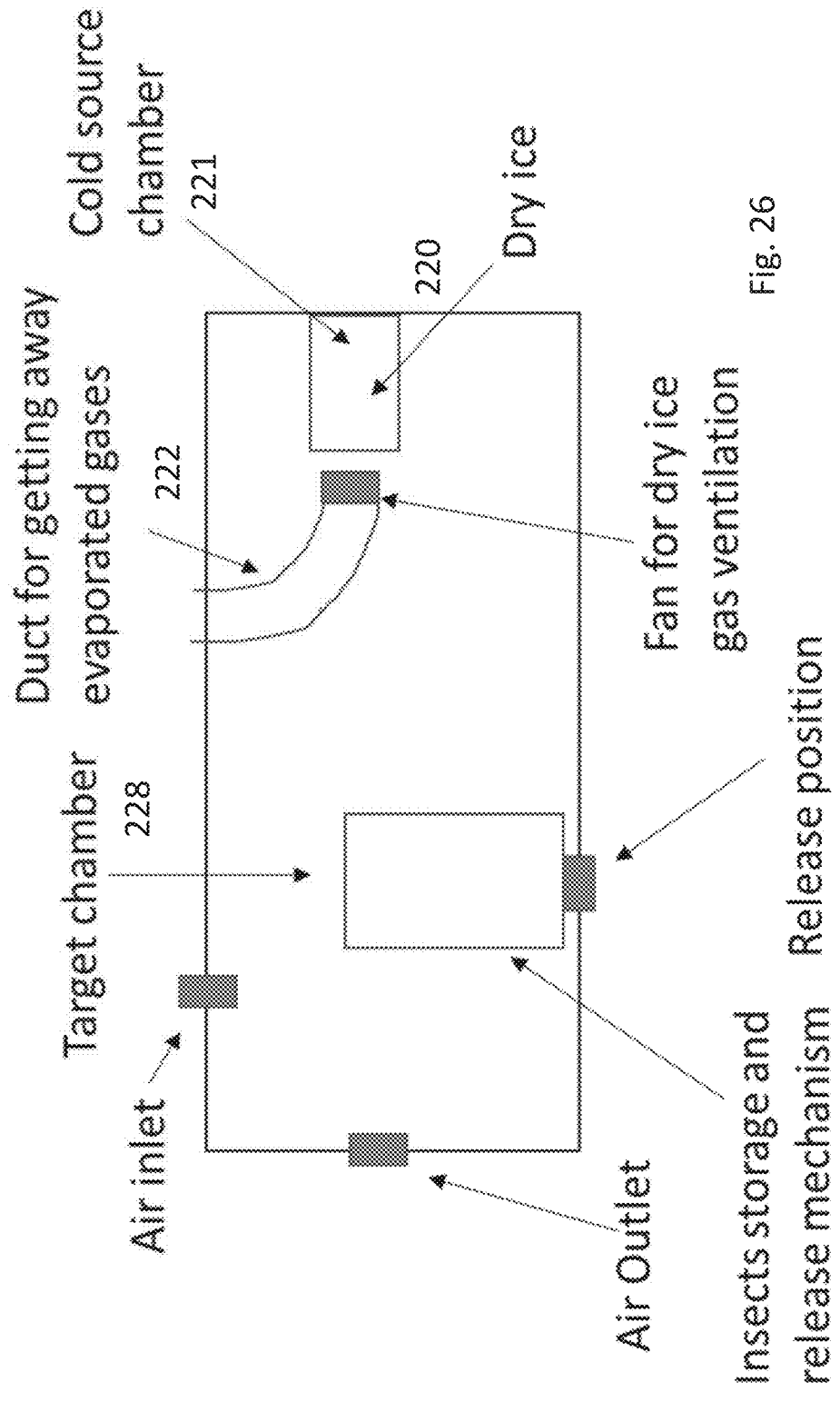
FIG. 26 is a view of a cold source chamber and target chamber showing ventilation details to prevent the insects from being harmed by $CO_2$ from the dry ice.

FIG. 26 is a view from above showing an arrangement for managing the dry ice 220 located in cold source chamber 221. A duct 222 is provided to guide the evaporated gas away from the dry ice and away from the insects may be added as depicted below. A fan 224 for dry ice gas ventilation may be provided to assist with the removal of harmful gases so as to keep them away from the insects in target chamber 228. The use of a duct to guide the dry ice or guidance of cold air may be applied to any of the examples and embodiments herein.

In embodiments, instead of using dry ice, ice cubes or ice packs or liquid nitrogen or other sources of cold temperature may be used. Dry ice has an advantage because of its light weight and its ability to last for many hours, however other solutions are possible in suitable circumstances.

Figure 27:
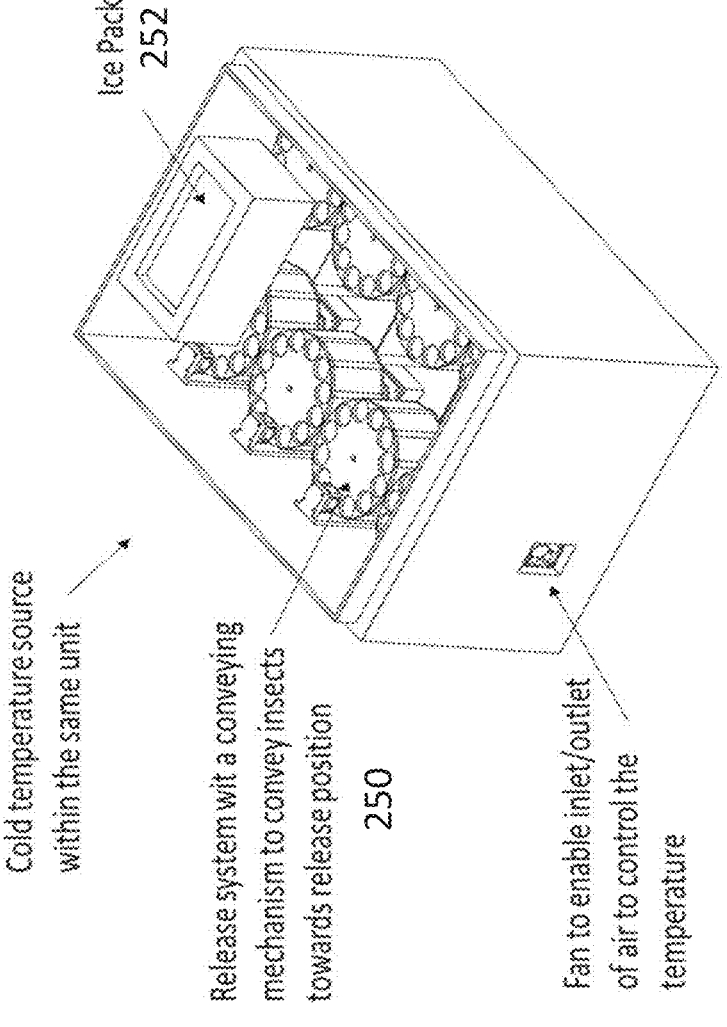
FIG. 27 is a simplified view from above of an embodiment using a cold temperature source within the insect release chamber.

Regular water ice may be packed in ice packs or placed in an ice chamber. With regular ice the heat transfer unit may be optionally dispensed with. The regular ice does not produce harmful amounts CO2 as dry ice does. Water ice is heavier than dry ice, but may provide a low temperature for a longer time, however the resulting melt water may need to be managed. FIG. 27 is a simplified perspective view of a target chamber 250 having a release system based on the carousel concept, and a regular ice pack 252 without isolation, barrier or heat transfer unit between the two.

In FIG. 27, ice is located within the same chamber the insects are located, however the temperature control of the previous embodiments may continue to apply.

In this disclosure the term "pupae" may also refer in this document to an individual pupa depending on the context. The term "permeable" refer to materials which allows liquid to flow, leak or flush through it, such as permeable or porous surfaces. The heat transfer surface may be a surface made of multiple surfaces or a single surface, and may be of different shapes, for example square, rounded, continuous or a permeable surface, or it may be made a rod or a tube or a plate or a series of rods, with the ability to transfer heat. Immobilized insects may refer to stationary insects, sedated insects, and or to insects who are incapable of flying and this may be due to cool temperatures selected as suitable for the individual species of insect. Canisters, tubes, cans, release can, release canister, release tube, and like terms may be used to describe the same functionality depending on the context in the sentence.

The present embodiments generally separate the area where insects are kept from the source of chilling, which is dry ice, all being mounted on a drone which flies, so that the temperature of the insects is kept low and regulated during flight, and the insects are then automatically and controllably released during the flight.

Figure 28:
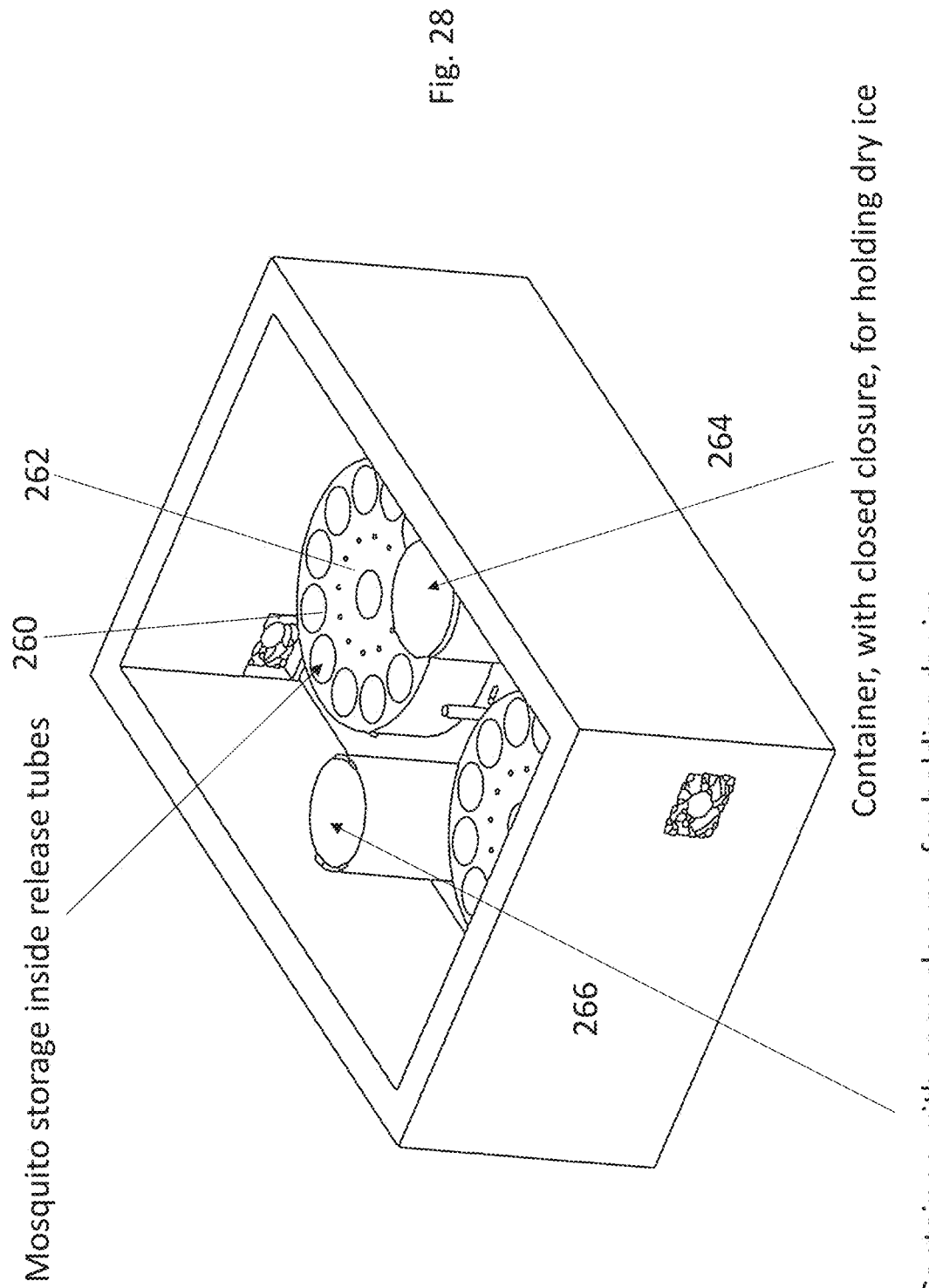
FIG. 28 is a simplified view of an alternative embodiment using a cold temperature source located within the insect release chamber.

Referring now to FIG. 28, mosquitoes are held inside canisters 260 on a carousel 262 as before. The dry ice may be kept inside containers such as closed container 264 and open container 266. The containers are in the same chamber as the insects are located. Containers 264 and 266 may have holes below or above to guide the gas away from the insects.

Reference is now made to FIG. 29, which shows a system 270 for two-step cooling. The dry ice 272 is kept in a dry ice compartment 274 on a cold transfer surface 276. On the other side of cold transfer surface 276 is an intermediate cold chamber 278. Fans 280 are used to blow air from the intermediate cold chamber to a regulated temperature chamber 282, which forms the insect chamber where the insects are in canisters or the like on a release mechanism such as the carousels 284 of the previous embodiments. More specifically, the dry ice cools a surface which then causes an intermediate chamber connected with that surface to be chilled. Then at the surface of the middle area there are fans which direct air towards the insects, which air does not contain harmful $CO_2$ from the dry ice.

Figure 30:
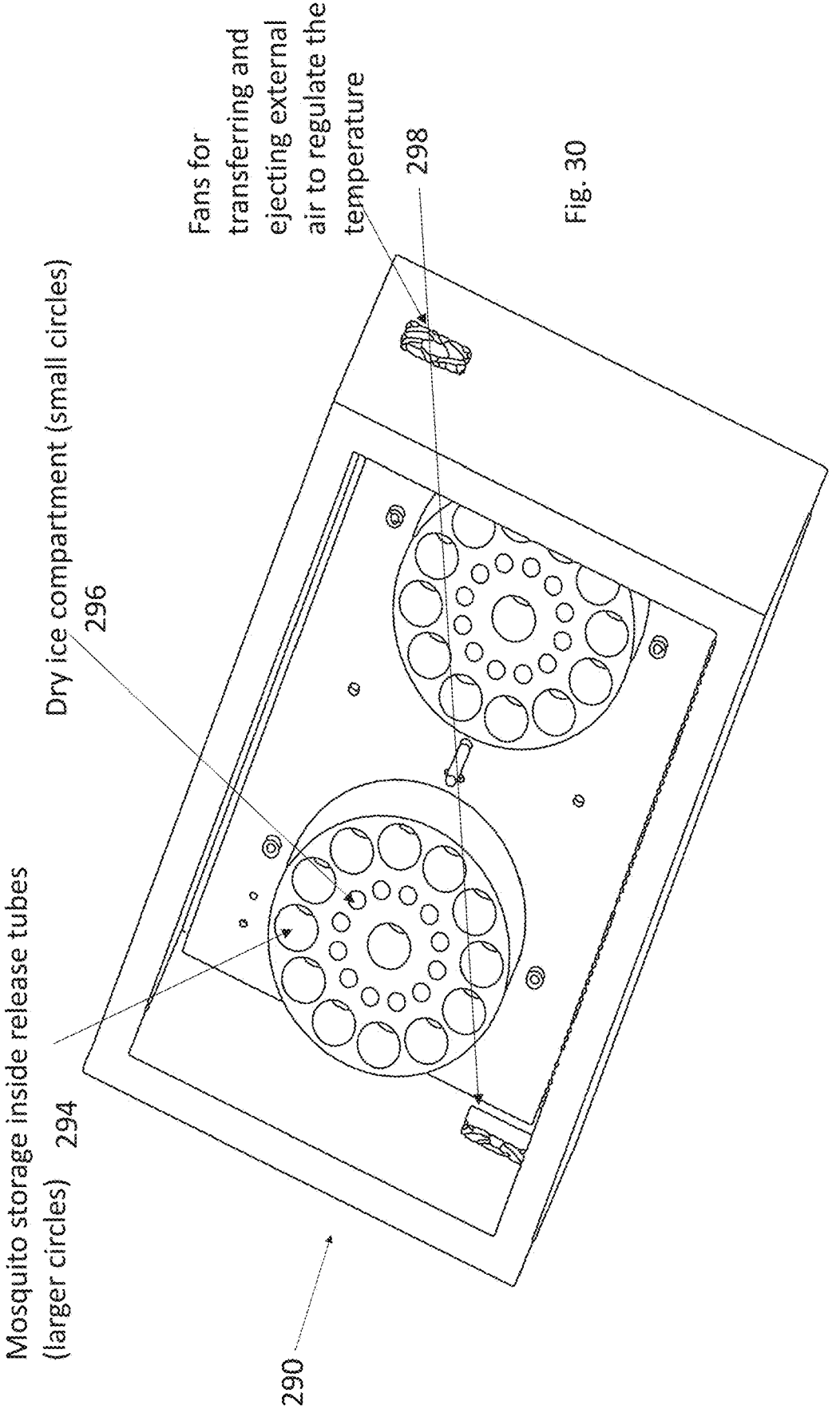
FIG. 30 is a simplified view of a further alternative embodiment using a cold temperature source located within the insect release chamber and with fans to further regulate the temperature.

Reference is now made to FIG. 30 which shows a carousel-based insect release system 290 where numerous small dry ice compartments 292 are laid out on the carousels 294 themselves. Fans 296 provide temperature regulation.

Figure 31:
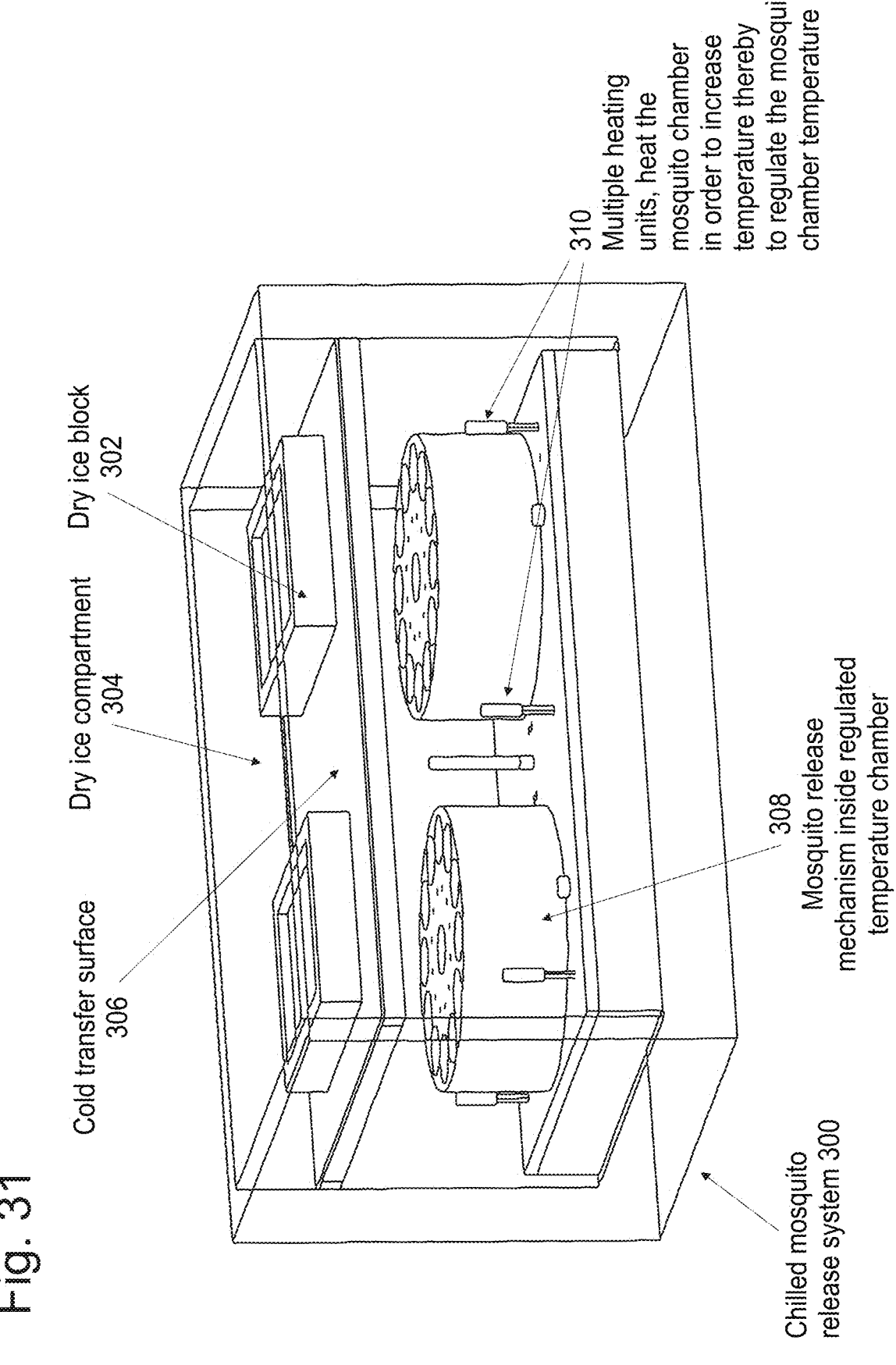
FIG. 31 is a simplified view of an embodiment of the present invention in which heating units are used with the cold source to regulate the temperature.

Reference is now made to FIG. 31, which shows a further embodiment of the present invention, in which temperature regulation is carried out by operating heaters together with the cold source. The system 300 includes a cold chamber or dry ice compartment 302 with a dry ice block 304 and a cold transfer surface 306 as before. The mosquito release system is made of carousels 308 as before and multiple heating units 310 heat the mosquito chamber when needed to keep the temperature at the control point. More specifically, instead of using fans at the exterior in order to increase the temperature, heating source elements are used. Such heating elements may comprise heating pads, PTC (Positive temperature coefficient) devices, light bulbs that emit heat, heating resistors that emit heat or other available devices that emit heat When the temperature is too low, the elements are turned on, and when the temperature rises above a specified threshold, they (one or many) are turned off. Hence, there is no need for fans to propel hotter air from the outside, or constant opening to the outside, and the entire unit other than the mosquito ejection points, is more closed. Problems due to units being too close together and blocking air flow are avoided, since there is no dependency on external airflow. Also, as this approach does not rely on external conditions, it is less sensitive to the outside temperature.

In order to achieve as homogenous temperature as possible within the insect chamber, at least one internal fan can be mounted within the insect chamber to circulate the air inside the insect chamber. Such an internal fan may be combined with a heating element and serve as the heating element in an alternative embodiment to that described in respect of FIG. 31. In such a case, the fan emits heat and the air blown from the fan circulates the hot air inside the chamber to achieve better temperature distribution within the chamber, without the need for fans propelling hot air from the outside. Such fans may be for example PTC fans.

Figure 32:
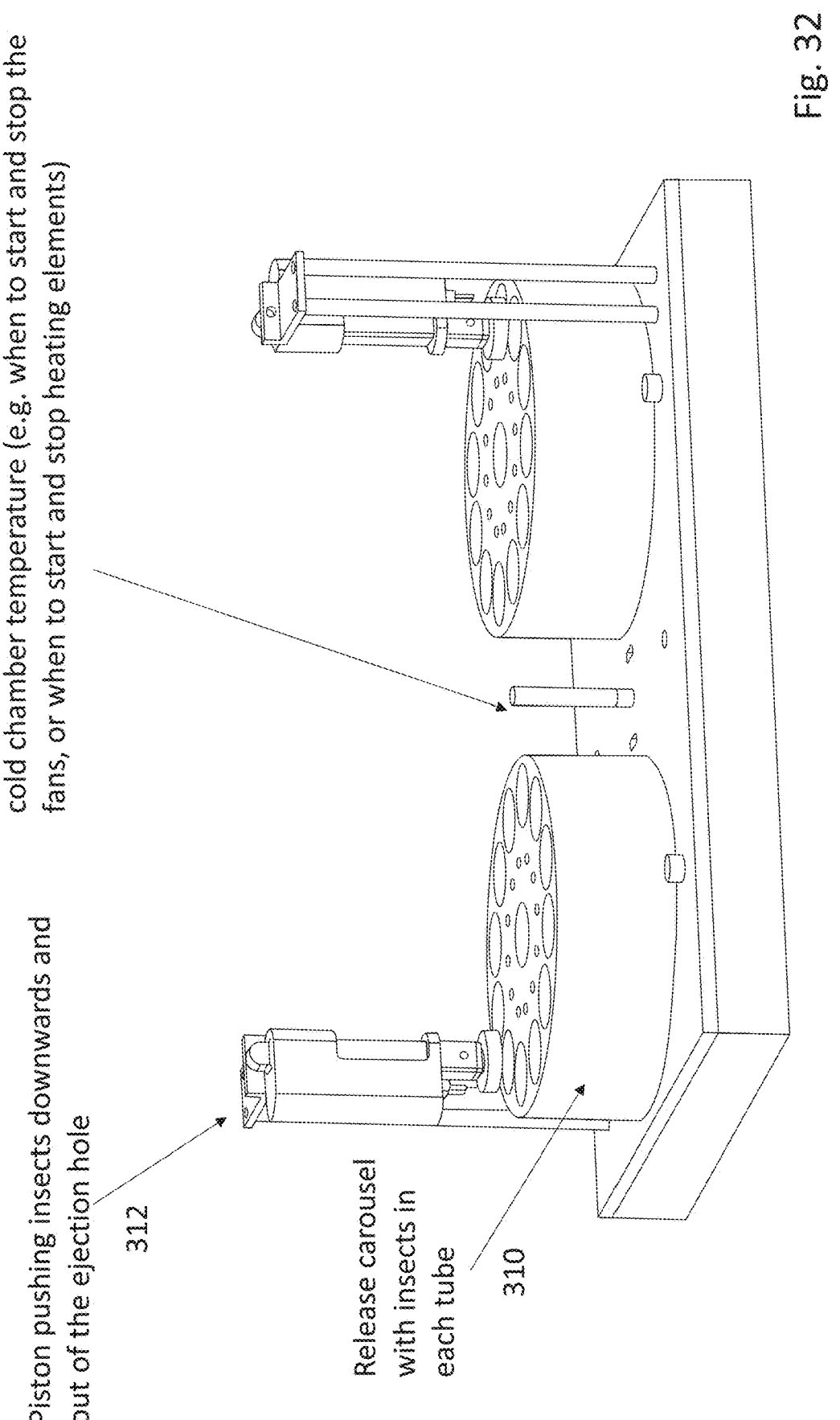
FIG. 32 is a simplified view of an embodiment in which a piston is used to expel insects.

Reference is now made to FIG. 32, which illustrates use of a piston to expel insects from the canisters in which they are stored. The carousel 310 rotates as before so that the canisters get into position one by one at the release point which under the piston 312. The piston pushes insects downwards and out through the ejection hole.

There are various ways to push a material.

Figure 33:
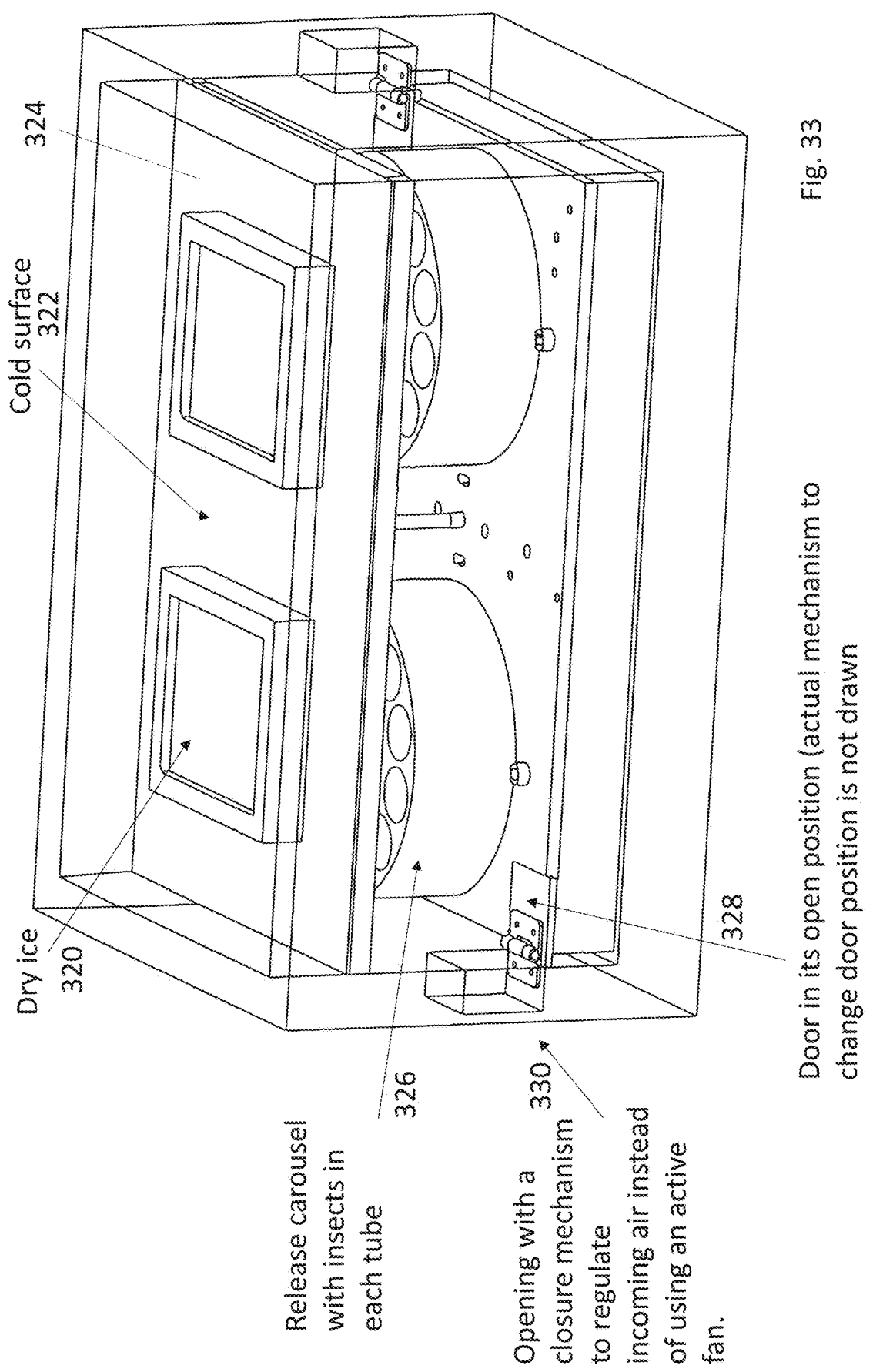
FIG. 33 is a simplified view of an embodiment in which a closable opening is used to regulate temperature.

Reference is now made to FIG. 33, which illustrates temperature regulation by means of opening and closing a door. Instead of controlling the temperature by having a fan to control entry of air, a door may be closed and opened. In FIG. 33, the dry ice 320 and cold surface 322 of cold chamber 324 operate as before. The insects are on a release carousel 326 and a door 328 covers an opening 330 which has a closure mechanism to controllably open and close the door as the temperature falls.

Figure 34:
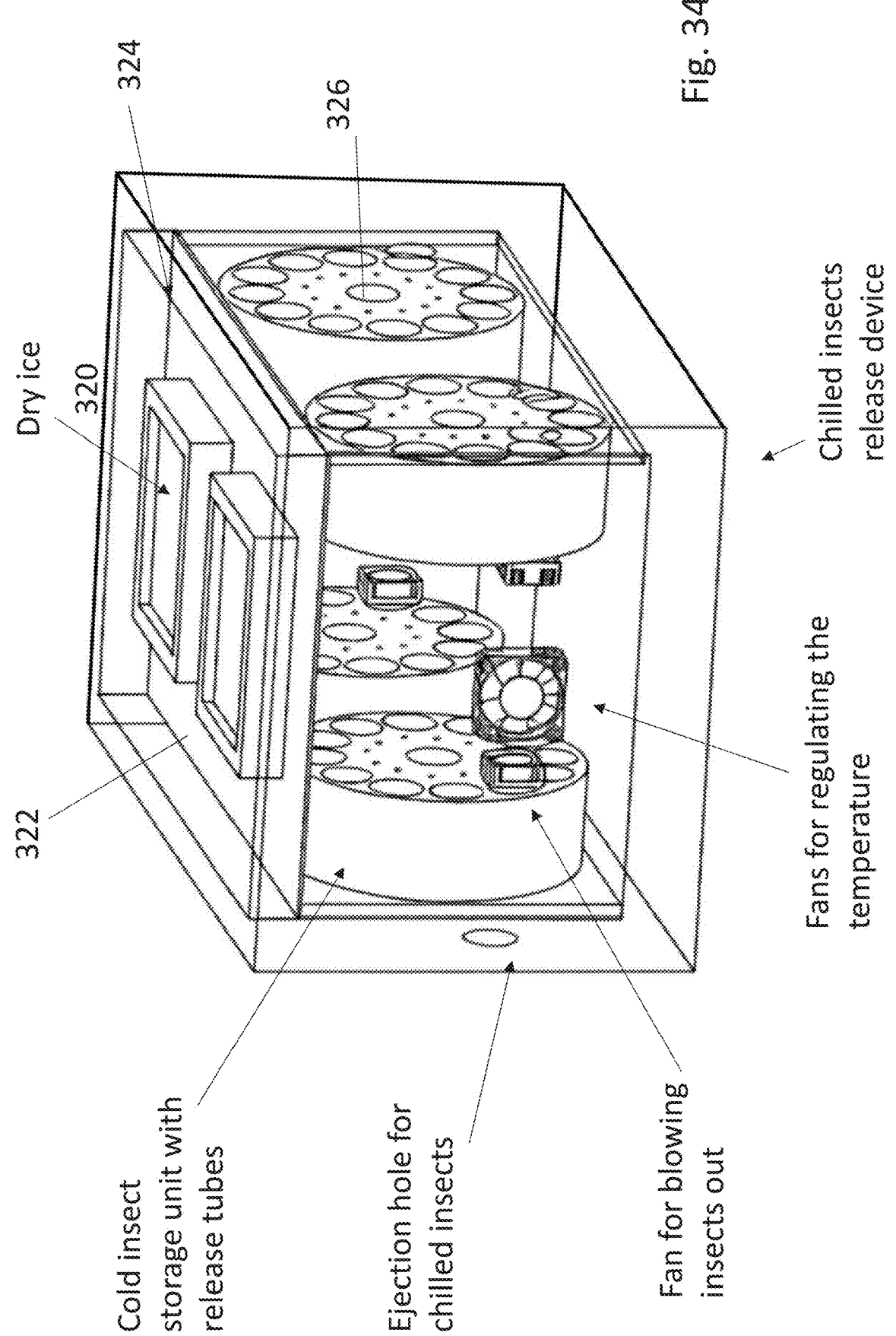
FIG. 34 is a simplified view of an embodiment of the present invention in which the carousels are mounted vertically.

Reference is now made to FIG. 34, in which the orientation of the insect cartridges is vertical. The dry ice 320 and cold surface 322 of cold chamber 324 operate as before. The insects are on a release carousel 326, however the carousels are in a vertical orientation and instead of ejecting the insects downwards, they are ejected sideways, with advantages of certain space utilization.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment and the present description is to be construed as if such embodiments are explicitly set forth herein. Conversely, various features of the invention, which are, for brevity, described in the context of a single embodiment, may also be provided separately or in any suitable subcombination or may be suitable as a modification for any other described embodiment of the invention and the present description is to be construed as if such separate embodiments, subcombinations and modified embodiments are explicitly set forth herein. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An insect distribution device for carrying by drone to distribute insects from the air, the device comprising:
   a source of passive cooling;
   an insect chamber;
   at least one insect compartment in said insect chamber;
   at least one release point; wherein the source of passive cooling is in thermal contact with the insect chamber to keep said at least one insect compartment below a predetermined temperature, said predetermined temperature selected to keep said insects passive during storage, the device being configured to cause said at least one insect compartment to reach said release point for aerial release, wherein said source of passive cooling is dry ice, and said dry ice is vented to the outside to divert carbon dioxide away from said insects.

2. The insect distribution device of claim 1, comprising a cooling chamber, said source of passive cooling being located in said cooling chamber.

3. The insect distribution device of claim 2, said cooling chamber having a thermal conductor, said thermal conductor extending from within said cooling chamber to within said insect chamber.

4. The insect distribution device of claim 2, wherein said cooling chamber has a mutual wall with said insect chamber, said mutual wall comprising a thermal conductor.

5. The insect distribution device of claim 3, wherein said thermal conductor comprises aluminum.

6. The insect distribution device of claim 1, comprising a controller, the controller configured to control the temperature around said insects by ventilating said insect chamber when said insect chamber temperature falls below a predetermined minimum value, and/or stopping said ventilating when said insect chamber temperature reaches a predetermined maximum value.

7. The insect distribution device of claim 1, comprising a controller, the controller configured to control the temperature around said insects by switching on heating elements when said insect chamber temperature falls below a predetermined minimum value and/or switching off said heating elements when said temperature exceeds a predetermined maximum value.

8. The insect distribution device of claim 1, comprising at least one carousel, the carousel comprising a plurality of said insect compartments, the carousel having a respective release point, the insect compartments to arrive one by one at said release point as said carousel rotates.

9. The insect distribution device of claim 1, wherein said release point comprises an open floor, the insects falling through the floor as the release point is reached, or said release point comprises a closable opening, the closable opening configured to be open when an insect compartment is present to release said insects.

10. The insect distribution device of claim 8, wherein the carousel has a variable rotation rate.

11. The insect distribution device of claim 1, the release point comprising a closable opening, the closable opening configured to be open when an insect compartment is present to release said insect compartment.

12. The insect distribution device of claim 8, wherein said insect compartment comprises a cavity built into a conveyance unit.

13. The insect distribution device of claim 8, wherein said insect compartment comprises a cylinder.

14. The insect distribution device of claim 1, further comprising an actuator, the actuator configured to apply a knock or vibration to an insect compartment at said release point to ensure effective insect release.

15. The insect distribution device of claim 1, further comprising a release chamber beneath the release point into which insects from said insect compartment are dropped prior to release.

16. The insect distribution device of claim 15, further comprising a heating unit in association with said release chamber to warm up said insects.

17. The insect distribution device of claim 16, further comprising a shutter at an outlet of said release chamber, said shutter configured to be opened following a predetermined time delay after said insects are dropped in from said heating container, said predetermined time delay being selected to give time to said heating chamber to heat said insects sufficiently to make them more active.

18. A drone carrying the insect distribution device of claim 1.

19. A method for aerial release of insects, comprising:
loading said insects into a plurality of insect compartments;
loading said compartments onto a feeding system, the feeding system being configured to feed said plurality of compartments to a release point;
placing a passive cooling element in thermal contact with said feeding system or a chamber containing said feeding system;

loading said feeding system and said passive cooling element onto a drone;
controllably releasing said insects from said drone by feeding said insect compartments to said release point and releasing, wherein said passive cooling element comprises dry ice, the method comprising venting said dry ice to the outside to divert carbon dioxide away from said insects.

20. The method of claim 19, wherein said insects are released at said release point.

21. The method of claim 19, wherein said insect containers are released at said release point.

22. The method of claim 19, comprising using said passive cooling element together with a warming procedure to keep said chamber containing said feed system within upper and lower bounds of a preset temperature.

23. The method of claim 22, wherein said warming procedure comprises one member of the group of opening the chamber to outside air, operating fans and operating warming elements.

24. The method of claim 19, further comprising applying a vibration or a knock or puffing to ensure release of said insects.

25. The method of claim 24, comprising varying a strength of said knock or a duration or strength of said vibrations or duration and velocity of puffing air.

26. An insect distribution device for carrying by drone to distribute insects from the air, the device comprising:
a source of passive cooling;
an insect chamber;
at least one release zone; wherein the source of passive cooling is in thermal contact with the insect chamber to keep said insects below a predetermined temperature, said predetermined temperature selected to keep said insects passive during storage, the device being configured to cause said insects to reach said release zone for aerial release, wherein said source of passive cooling is dry ice, and said dry ice is vented to the outside to divert carbon dioxide away from said insects.

27. A method for aerial release of insects, comprising:
loading said insects into at least one insect chamber;
loading said chamber onto a feeding system, the feeding system being configured to feed said insects to a release zone;
placing a passive cooling element in thermal contact with said feeding system or a chamber containing said feeding system;
loading said feeding system and said passive cooling element onto a drone; and
controllably releasing said insects from said drone by feeding said insects to said release zone, wherein said passive cooling element comprises dry ice, the method comprising venting said dry ice to the outside to divert carbon dioxide away from said insects.

\* \* \* \* \*